(12) United States Patent
Kazerooni et al.

(10) Patent No.: US 8,070,700 B2
(45) Date of Patent: *Dec. 6, 2011

(54) LOWER EXTREMITY ENHANCER

(75) Inventors: Homayoon Kazerooni, Berkeley, CA (US); Jean-Louis Racine, Rockville, MD (US); Andrew Chu, Berkeley, CA (US); Adam Zoss, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 12/622,362

(22) Filed: Nov. 19, 2009

(65) Prior Publication Data

US 2010/0204627 A1    Aug. 12, 2010

Related U.S. Application Data

(63) Continuation of application No. 10/976,652, filed on Oct. 29, 2004, now Pat. No. 7,628,766.

(60) Provisional application No. 60/515,572, filed on Oct. 29, 2003.

(51) Int. Cl.
*A61F 5/00* (2006.01)
(52) U.S. Cl. .......... 602/16; 602/23; 602/26; 602/27
(58) Field of Classification Search ........... 602/5, 16, 602/19, 26, 27, 23; 601/33–35; 482/51, 482/66
See application file for complete search history.

(56) References Cited

U.S. PATENT DOCUMENTS

| | | | |
|---|---|---|---|
| 406,328 A | 7/1889 | Yagn | |
| 420,178 A | 1/1890 | Yagn | |
| 420,179 A | 1/1890 | Yagn | |
| 440,684 A | 11/1890 | Yagn | |
| 539,872 A | 5/1895 | Kheiralla | |
| 807,908 A | 12/1905 | Bradstreet | |
| 979,243 A | 12/1910 | Anderson | |
| 1,308,675 A | 7/1919 | Kelley | |
| 4,647,004 A | 3/1987 | Bihlmaier | |
| 4,872,665 A | 10/1989 | Chareire et al. | |
| 5,020,790 A | 6/1991 | Beard et al. | |
| 5,282,460 A | 2/1994 | Boldt | |
| 5,476,441 A * | 12/1995 | Durfee et al. | 602/23 |
| 5,658,242 A * | 8/1997 | McKay et al. | 602/16 |
| 5,662,693 A * | 9/1997 | Johnson et al. | 607/49 |
| 5,961,476 A | 10/1999 | Betto et al. | |
| 6,422,329 B1 | 7/2002 | Kazerooni et al. | |
| 6,500,210 B1 | 12/2002 | Sabolich et al. | |

(Continued)

OTHER PUBLICATIONS

"Exoskeleton Prototype Project: Final Report on Phase I," (Oct. 1966). Contract No. N00014-66-C0051, Mechanical Equipment Branch, Mechanical Technology Laboratory, Research and Development Center, General Electric Company: Schenectady, New York, pp. 1-72.

(Continued)

*Primary Examiner* — Michael A. Brown
(74) *Attorney, Agent, or Firm* — Diederiks & Whitelaw, PLC

(57) ABSTRACT

A lower extremity enhancer to be worn by a user includes two leg supports having a plurality of jointed links. Proximal ends of the leg supports are connected to a back frame. Distal ends of the leg supports are connected to two foot links. The leg supports are powered by a plurality of actuators adapted to apply torques to the leg supports in response to movement of the user's legs.

20 Claims, 19 Drawing Sheets

U.S. PATENT DOCUMENTS

| | | | |
|---|---|---|---|
| 6,676,707 | B2 | 1/2004 | Yih et al. |
| 6,807,869 | B2 | 10/2004 | Farringdon et al. |
| 6,821,233 | B1 | 11/2004 | Colombo et al. |
| 6,966,882 | B2 | 11/2005 | Horst |
| 7,048,707 | B2 | 5/2006 | Schwenn et al. |
| 7,111,704 | B2 | 9/2006 | Johnson |
| 7,135,003 | B2 | 11/2006 | Dariush |
| 7,153,242 | B2 | 12/2006 | Goffer |
| 7,217,247 | B2 | 5/2007 | Dariush |
| 7,390,309 | B2 | 6/2008 | Dariush |
| 7,396,337 | B2 | 7/2008 | McBean |
| 7,445,606 | B2 | 11/2008 | Rastegar |
| 7,537,573 | B2 | 5/2009 | Horst |
| 2004/0116839 | A1 | 6/2004 | Sarkodie-Gyan |
| 2004/0158175 | A1 | 8/2004 | Ikeuchi et al. |
| 2006/0046907 | A1 | 3/2006 | Rastegar et al. |
| 2006/0260620 | A1 | 11/2006 | Kazerooni et al. |
| 2007/0056592 | A1 | 3/2007 | Kazerooni et al. |

OTHER PUBLICATIONS

"Machine Augmentation of Human Strength and Endurance: Hardiman I Prototype Project." General Electric Company, Schenectady, New York, Jul. 1969.

"Research and Development Prototype for Machine Augmentation of Human Strength and Endurance: Hardiman I Project," (May 1971). ONR Contract No. N0014-66-C0051, Specialty Materials Handling Products Operation, General Electric Company, Schenectady, New York, pp. 1-25.

Arroyo, P. "Design of a Minimally Actuated Assistive Device." Graduate Thesis, UC-Berkeley Mechanical Engineering Dept., 1998.

Belforte, G., et al. "Pneumatic Active Gait Orthosis." Mechatronics, vol. 11, No. 3, pp. 301-323, Apr. 2001.

Clark, D.C. et al. "Exploratory Investigation of the Man Amplifier Concept." Technical Documentary Report No. AMRL-TDR-62-89, United States Air Force, Wright-Patterson Air Force Base, Ohio, Aug. 1962.

Ferris, D., et al. "An Ankle-foot Orthosis Powered by Artificial Muscles." Proceedings of the 25th Annual Meeting of the American Society of Biomechanics, San Diego, California, Aug. 2001.

Harley, J.A. "Design and Construction of an Underactuated Assistive Walking Device." Graduate Thesis, UC-Berkeley Mechanical Engineering Dept., Aug. 1995.

International Search Report and Written Opinion mailed Aug. 7, 2007, for PCT Application No. PCT/US06/01981 filed Jan. 18, 2006, 11 pages.

International Search Report and Written Opinion mailed Aug. 15, 2007, for PCT Application No. PCT/US06/14227 filed Apr. 13, 2006, 13 pages.

International Search Report and Written Opinion mailed Jan. 28, 2008, for PCT Application No. PCT/US07/06122 filed Mar. 9, 2007, 12 pages.

Irby, S., et al. "Automatic Control Design for a Dynamic Knee-Brace System." IEEE Transactions on Rehabilitation Engineering, vol. 7, No. 2, pp. 135-139, Jun. 1999.

Johnson, D., et al. "Development of a Mobility Assist for the Paralyzed, Amputee, and Spastic Patient." Proceedings of the Fifteenth Southern Biomedical Engineering Conference, IEEE, pp. 67-70, Dayton, Ohio, Mar. 1996.

Kasaoka, K., et al. "Predictive Control Estimating Operator's Intention for Stepping-up Motion by Exoskeleton Type Power Assist System HAL." Proceedings of the IEEE/RJS International Conference on Intelligent Robots and Systems (IROS), vol. 3, pp. 1578-1583, Maui, Hawaii, Nov. 2001.

Kawamoto, H., et al. "Power Assist System HAL-3 for Gait Disorder Person." Lecture Notes in Computer Science (LNCS), vol. 2398, Proceedings of the Eighth International conference on Computers Helping People with Special Needs (ICCHP), pp. 196-203, Berlin, Germany, 2002.

Kawamoto, H., et al. "Comfortable Power Assist Control Method for Walking Aid by HAL-3." Proceedings of the IEEE International Conference on Systems, man, and Cybernetics (SMC), vol. 4, Hammamet, Tunisia, Oct. 2002.

Lee, S. et al. "Power Assist Control for Walking Aid with HAL-3 Based on EMG and Impedance Adjustment around Knee Joint." Proceedings of the IEEE/RJS International Conference on Intelligent Robots and Systems (IROS), vol. 2, pp. 1499-1504, Lausanne, Switzerland, 2002.

Lim, Michael Zin Min, "An Analysis on the Performance of an Underactuated Lower Extremity Enhancer." Graduate Thesis, UC-Berkeley Mechanical Engineering Dept., 2000.

Misuraca, J., et al. "Lower Limb Human Muscle Enhancer." Proceedings of the Symposium on Advances in Robot Dynamics and Control, ASME International Mechanical Engineering Congress and Exposition (IMECE), New York, New York, Nov. 2001.

Mori, Y., et al. "Development of Straight Style Transfer Equipment for Lower Limbs Disabled." Proceedings of the IEEE International Conference on Robotics and Automation (ICRA), vol. 3, pp. 2486-2491, New Orleans, Louisiana, May 2004.

Morris, S., et al. "Shoe-integrated Sensor System for Wireless Gait Analysis and Real-Time Feedback." Proceedings of the Second Joint EMBS/BMES Conference, pp. 2468-2469, Houston Texas, Oct. 2002.

Mosher, R.S. "Handyman to Hardiman." Automotive Engineering Congress, Society of Automotive Engineers, Detroit, Michigan, Jan. 1967.

Naruse, K., et al. "Design of Compact and Lightweight Wearable Power Assist Device." Proceedings of ASME International Mechanical Engineering Congress and Exposition (IMECE), Washington D.C., Nov. 2003.

Pratt, J., et al. "The RoboKnee: an Exoskeleton for Enhancing Strength and Endurance During Walking." Proceedings of the IEEE International Conference on robotics and Automation (ICRA), vol. 3, pp. 2430-2435, New Orleans, Louisiana, May 2004.

Rehnmark, F.L. "Dynamic Simulation and Design of a Powered Underactuated Assistive Walking Device." Graduate Thesis, UC-Berkeley Mechanical Engineering Dept., 1997.

Van Den Bogert, A. "Exotendons for Assistance of Human Locomotion." Biomedical Engineering Online, vol. 2, Oct. 2003.

Vukobratovic, M., et al. "Development of Active Anthropomorphic Exoskeletons." Medical and Biological Engineering, pp. 66-80, Jan. 1974.

Yamamoto, K., et al. "Development of Power Assisting Suit for Assisting Nurse Labor." JSME International Journal Series C., vol. 45, No. 3, Sep. 2002.

Yamamoto, K., et al. "Development of Power Assisting Suit (Miniaturization of Supply System to Realize Wearable Suit)." JSME International Journal Series C., vol. 46, No. 3, Sep. 2003.

\* cited by examiner

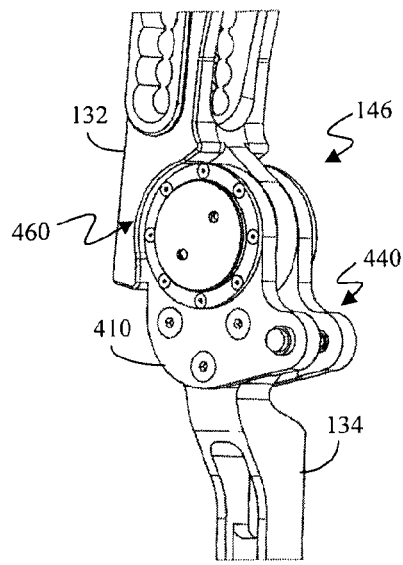 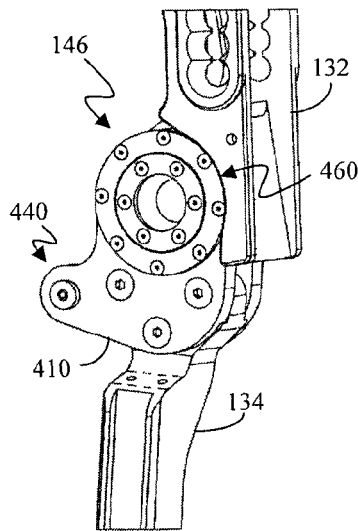
Fig. 4B            Fig. 4C
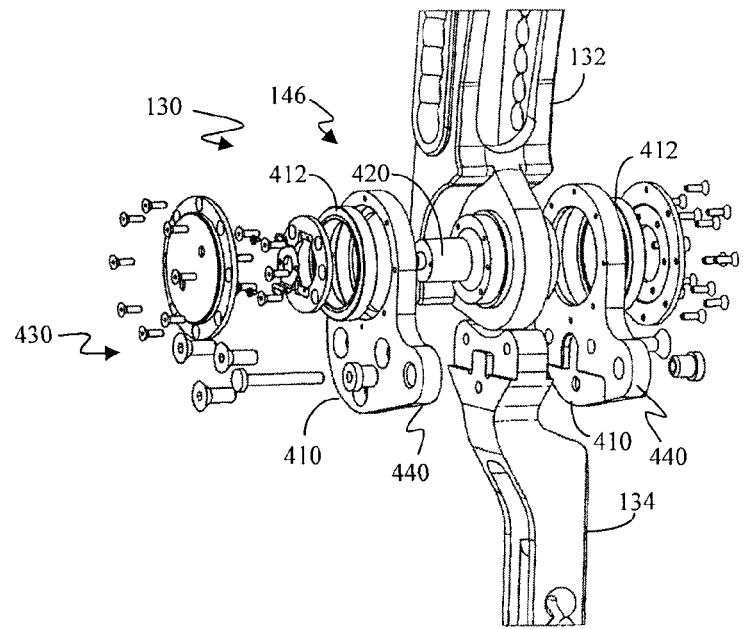
Fig. 4A

LOWER EXTREMITY ENHANCER

CROSS-REFERENCE TO RELATED APPLICATIONS

This application is a Continuation of U.S. patent application Ser. No. 10/976,652, filed Oct. 29, 2004, which claims the benefit of U.S. Provisional Application No. 60/515,572, titled LOWER EXTREMITY ENHANCER, filed Oct. 29, 2003, the entire contents of which are incorporated herein by reference for all purposes.

STATEMENT REGARDING FEDERALLY SPONSORED RESEARCH OR DEVELOPMENT

This invention was made with government support under Contract No. DAAD19-01-1-0509 awarded by Defense Advanced Research Projects Agency (DARPA). The government has certain rights in the invention.

BACKGROUND

1. Field

The present application relates to a robotic exoskeleton, and, more particularly, to a lower extremity enhancer to be worn by a user to enable the user to carry a load.

2. Related Art

A robotic exoskeleton to be worn by a user has been mostly the subject of science fiction. Attempts have been made to build a lower limb exoskeleton for both performance augmentation and rehabilitation purposes. In general, these attempts relied on an interpretation of muscle activity to prescribe a motion to the joints of the exoskeleton, or on a conscious command signal from the user, or were limited to a fixed set of predetermined physical activities. In general, the user of these exoskeletons was required to hold onto a walking aid when using the exoskeletons.

SUMMARY

In one exemplary embodiment, a lower extremity enhancer to be worn by a user includes two leg supports having a plurality of jointed links. Proximal ends of the leg supports are connected to a back frame. Distal ends of the leg supports are connected to two foot links. The legs supports are powered by a plurality of actuators adapted to apply torques to the leg supports in response to movement of the user's legs.

DESCRIPTION OF DRAWING FIGURES

The present application can be best understood by reference to the following description taken in conjunction with the accompanying drawing figures, in which like parts may be referred to by like numerals:

FIG. 4A is an exploded view of a jointed link;

FIGS. 4B and 4C are perspective views of the jointed link of FIG. 4A;

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Overview

Figure 1:
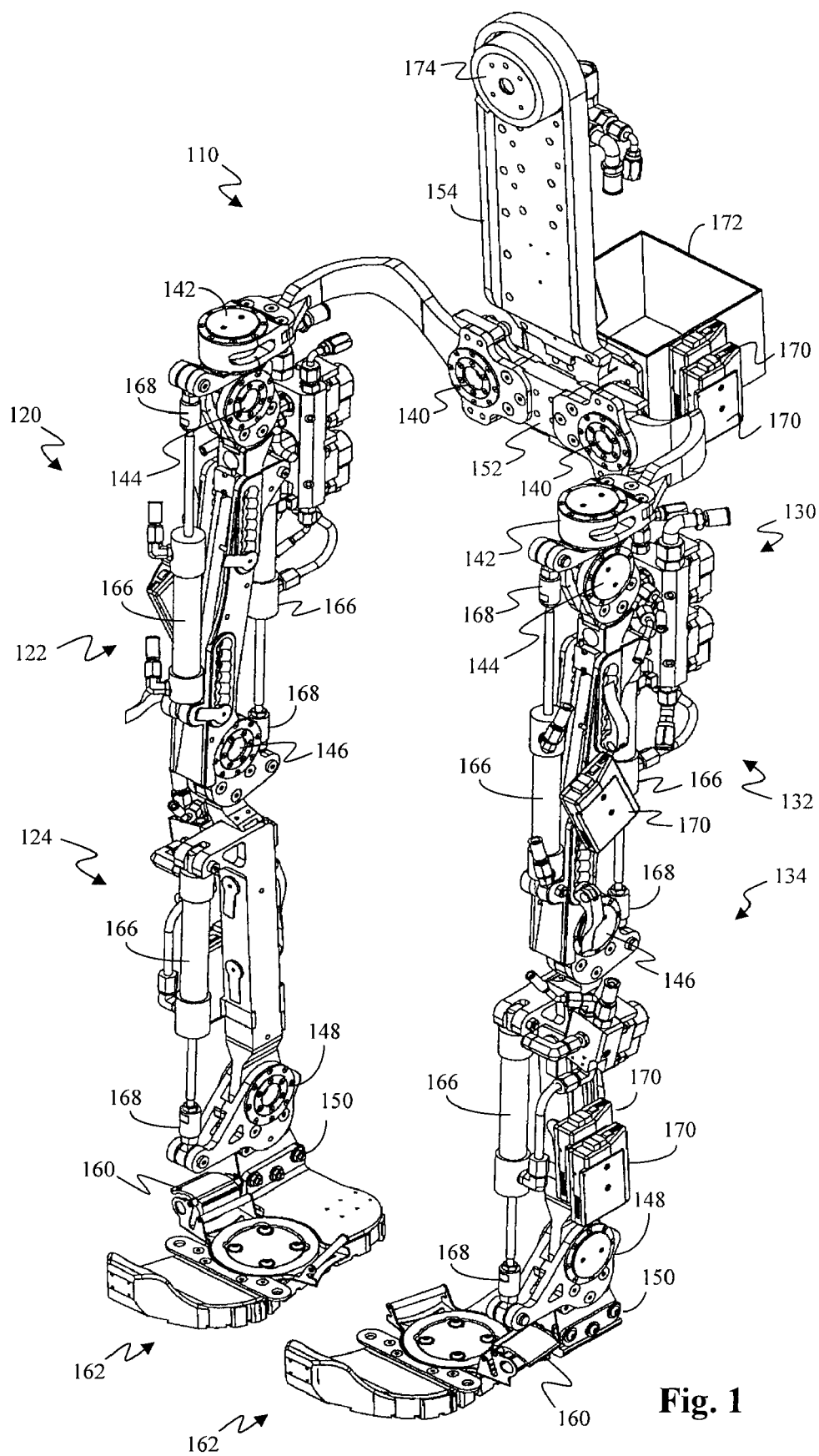
FIG. 1 is a schematic view of an exemplary lower extremity enhancer.

With reference to FIG. 1, in one exemplary embodiment, a lower extremity enhancer (hereinafter referred to as an "enhancer") 110 is adapted to be worn by a user to enable the user to carry a load. In the present exemplary embodiment, enhancer 110 includes two leg supports 120, 130 (right leg support 120 and left leg support 130) having multiple jointed links 122, 124, 132, and 134. A back frame 154, which carries the load, is connected to proximal ends of leg supports 120, 130. Two foot links 162 are connected to distal ends of leg supports 120, 130. Actuators 166 are adapted to apply torque to leg supports 120, 130.

Enhancer 110 includes multiple articulating joints that allow the movement of a user's lower extremities to be closely followed. In the present exemplary embodiment, right leg support 120 includes thigh link 122 and shank link 124 rotatably jointed and configured to move in flexion and extension at a knee joint 146. Left leg support 130 includes thigh link 132 and shank link 134 rotatably jointed and configured to move in flexion and extension at knee joint 146.

Foot links 162 and shank links 124, 134 are rotatably jointed and configured to move in flexion and extension at ankle joints 148. Foot links 162 can be rigidly and releasably attached to a user's feet. The regions of foot links 162 that contact the user's feet may include releasable bindings or fasteners 160 to connect to the user's feet or shoes. Other methods of attachment to the user's feet are also contemplated, including direct attachment (for example, by wearing a pair of "shoes" incorporated as part of enhancer 110), straps or buckles, and the like.

Back frame 154 and thigh links 122, 132 are rotatably jointed and configured to move in flexion and extension at hip joints 144. Back frame 154 and thigh links 122, 132 are also rotatably jointed and configured to move in abduction and adduction at hip joints 140. Back frame 154 and thigh lines 122, 132 are rotatably jointed and configured to move in rotation at hip joints 142. In FIG. 1, hip joints 142 are connected to a hip assembly 152, which is shown connected to back frame 154. It should be recognized, however, that hip assembly 152 can be integral to back frame 154.

Back frame 154 can include connections to a load, or to other components of enhancer 110, such as a power supply or control system. The user is also preferably attached to at least a portion of back frame 154. This attachment may be direct (e.g., strapping the user directly to back frame 154) or indirect (e.g., incorporating a detachable harness worn by the user, which engages back frame 154). For ease of use, both the foot attachments and the back attachments may be readily released by the user.

Enhancer 110 is adjustable to fit a wide variety of user body shapes and sizes. Quick adjustments may be made to shorten or extend the length of thigh links 122, 132, the length of shank links 124, 134, and the width of hip assembly 152 (waist). Further, the fixed attachment sites at the foot and back may also be adjusted to fit a variety of users. Alternatively, enhancer 110 can be fabricated to the precise dimensions of a particular user (or narrow class of users).

Enhancer 110 may also be designed to be easily disassembled for either storage or transport. For example, leg supports 120, 130 may be detachable.

Figure 2:
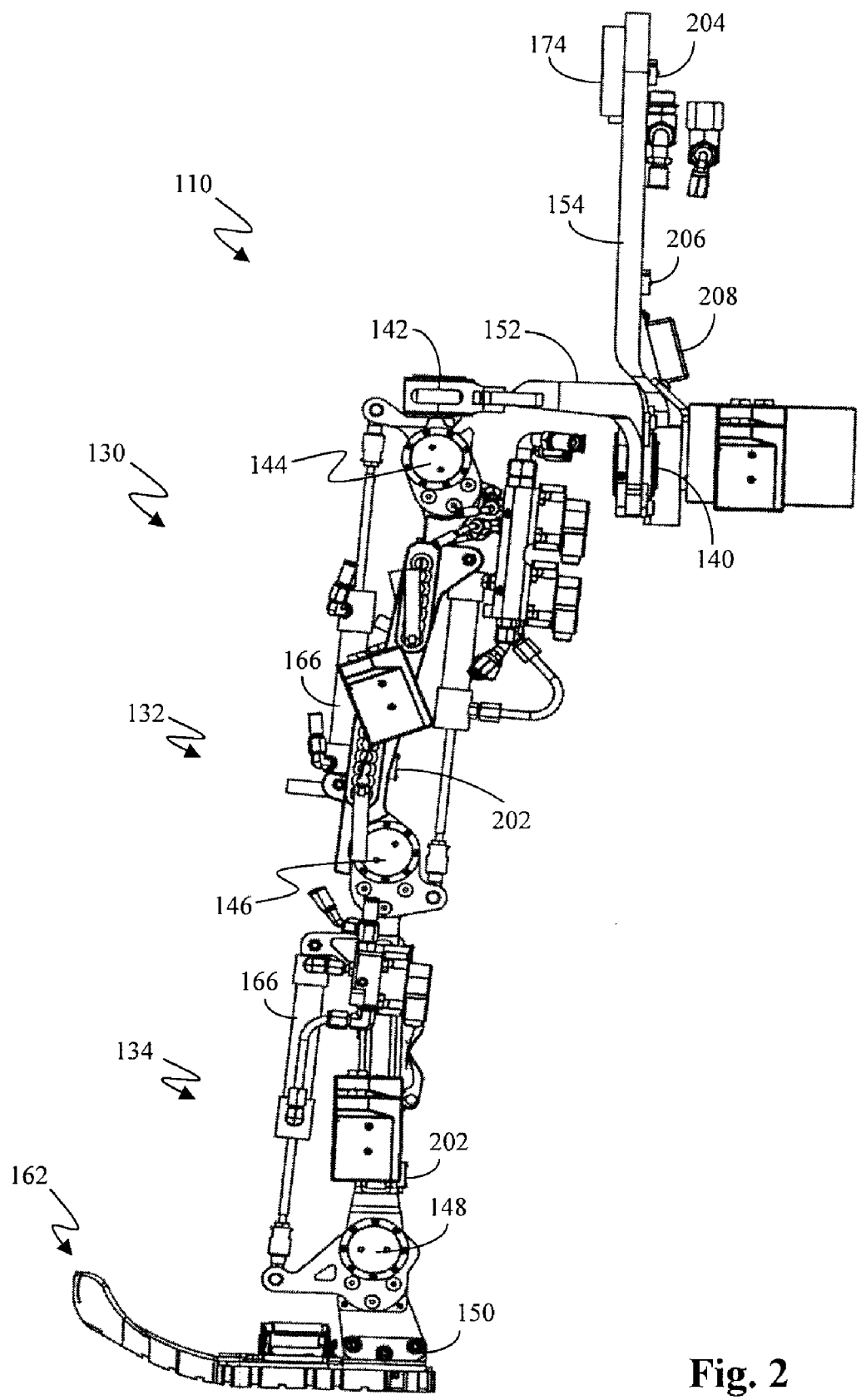
FIG. 2 is a schematic perspective view of a single leg support.

FIG. 2 shows a side perspective of left leg support 130. As depicted in FIG. 2, foot link 162 connects to an ankle region at the distal end of shank link 134. The ankle region shown has two articulated joints (an actuated flexion/extension ankle joint 148 and a passive abduction/adduction ankle joint 150). The shank link 134 connects to thigh link 132 at knee joint 146 configured to move in flexion/extension. Thigh link 132 connects to hip assembly 152, which includes three joints (hip joint 142 configured to move in rotation, hip joint 140 configured to move in abduction/adduction, and hip joint 144 configured to move in flexion/extension).

Figure 3:
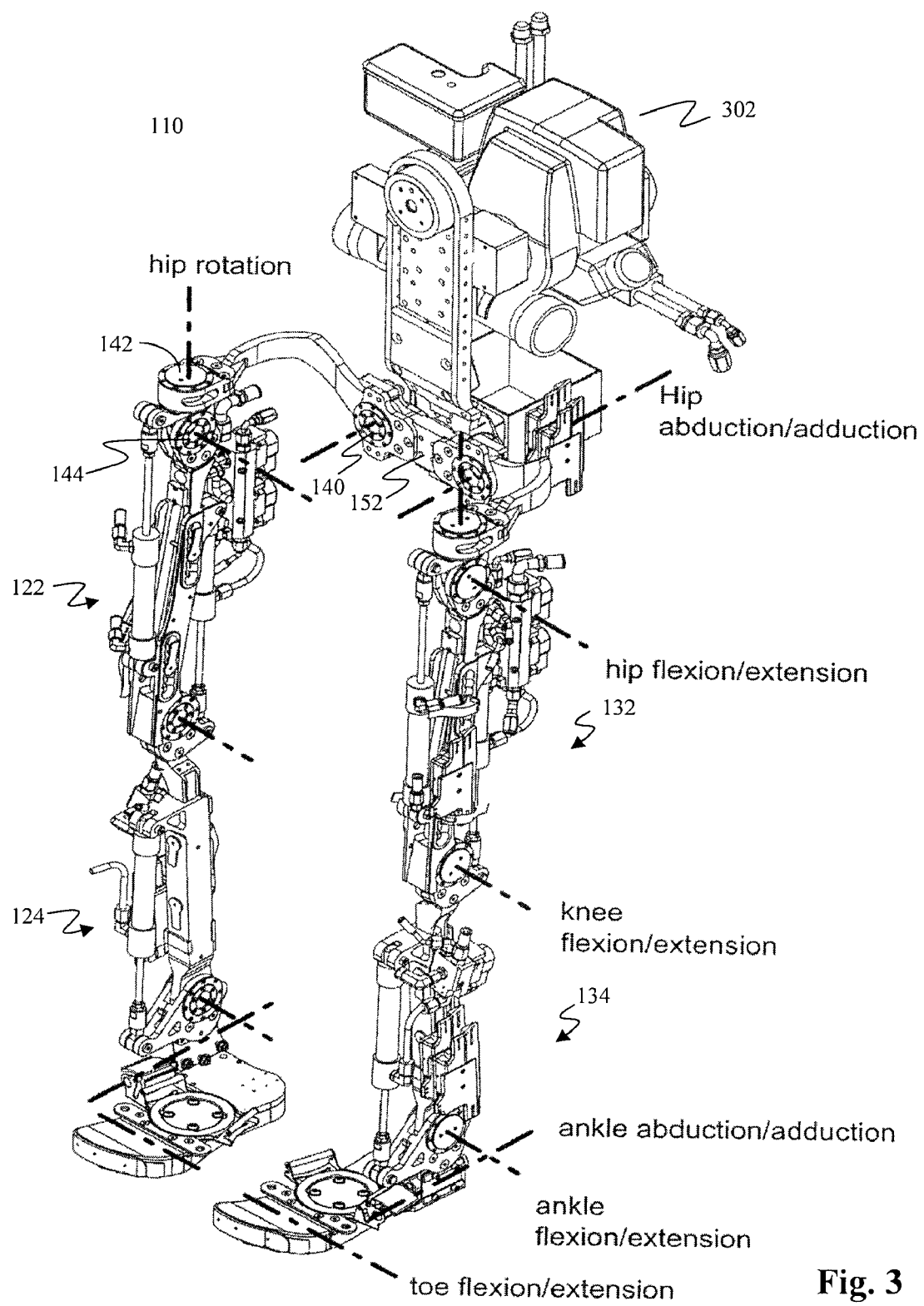
FIG. 3 is a perspective view of a lower extremity enhancer showing the degrees of freedom of some of the jointed links.

In the present exemplary embodiment, the joints of enhancer 110 correspond to joints of the user. As an example, FIG. 3 shows a schematic of enhancer 110 with seven degrees of freedom on each leg support, labeled: hip flexion/extension, hip rotation, hip abduction/adduction, knee flexion/extension, ankle abduction/adduction, ankle flexion/extension, and toe flexion/extension. Each degree of freedom corresponds to a single joint. These seven degrees of freedom are a subset of the degrees of freedom possible in most human lower extremities. Enhancer 110 can incorporate all of the degrees of freedom possible in a human lower extremity, or it may incorporate a subset of them. In particular, enhancer 110 can include the hip flexion/extension, the knee flexion/extension, and the ankle flexion/extension joints. Enhancer 110 embodied in FIG. 1 incorporates all seven of the degrees of freedom (and thus seven joints) illustrated in FIG. 3.

While enhancer 110 shown in FIGS. 1 to 3 closely corresponds to the anatomy of the human lower extremity region (for example, the degrees of freedom described for the joints of enhancer 110 roughly correlate to the degrees of freedom of the human hip, knee, and ankle joints), this correspondence is not a requirement. Thus, for example, a human hip joint is a ball-and-socket joint in which the upper leg is moved in flexion/extension, rotation, and abduction/adduction by a single joint. Further, all of these joints have the same axis of rotation. As shown in FIGS. 1 to 3, thigh links 122, 132 move in these directions by using three joints connected in series (hip joints 140, 142, and 144).

With reference to FIG. 1, in the present exemplary embodiment, some or all of the joints may be actively controlled or powered by actuators 166. Actuators 166 may be of any type that is capable of controllably moving a joint, such as electric motors, hydraulic motors, pneumatic motors, and the like. For example, FIG. 1 shows hydraulic actuators connected to a subset of the joints. Actuators 166 may have a control input (e.g., an electrical control input) and a power input corresponding to the type of actuator used at a given joint. In the case of hydraulic actuators, the power input is pressurized hydraulic fluid.

The exemplary embodiment of enhancer 110 illustrated in FIGS. 1 to 3 is powered at only the hip flexion/extension, the knee flexion/extension, and the ankle flexion/extension joints. It is possible, and may be desirable, to power additional joints. On the other hand, reducing the number of powered joints (and therefore the number of actuators) may also significantly reduce the weight and power requirements of enhancer 110.

In the present exemplary embodiment, sensors are used throughout enhancer 110 for detecting the position or status of enhancer 110 and the user. For example, sensors may detect: relative (or absolute) position of enhancer 110 and its components, the forces acting on enhancer 110 (particularly the joints), and the movement (e.g., velocity and acceleration) of the components. Sensors may be located anywhere on enhancer 110, particularly on and around the joints, actuators, links, and back frame. The sensors provide input into a control system, including a controller, which is configured to process the information and control the actuators.

In the present exemplary embodiment, enhancer 110 follows the motions of a user's lower extremities, shadowing the user's movements, and allowing the user to carry a load attached to back frame 154 without using a hand control. A user attached to enhancer 110 at the feet and back may walk, run, squat, bend, sit, swing from side to side, twist, climb, and maneuver on ascending and descending slopes.

Enhancer 110 may be worn and operated in both an "unpowered" and a "powered" state. When enhancer 110 is unpowered (meaning that the actuators are not actively actuating the joints), enhancer 110 passively follows the motions of the user's legs. In one exemplary embodiment, un-powered enhancer 110 supports loads in the vertical direction, while motion in the horizontal direction is provided by the user. Thus, the design of enhancer 110 may incorporate a number of variations in order to simplify use in the un-powered state. For example, the overall weight of enhancer 110 may be kept low by choosing low-weight materials, or by reducing the number of powered joints.

When enhancer 110 is "powered," movements are assisted by actuators 166, and follow a user's leg motions. In the "powered" state, slight user feedback on enhancer 110 causes actuators 166 to actuate the joints and assist with the motion. For example, a user walking while wearing a powered enhancer exerts torsion on enhancer 110, particularly at the joints. This torsion is detected by sensors, and used to calculate the appropriate force to be applied (e.g., at a joint) to assist the motion. The force applied by actuators 166 effectively reduces the impedance felt by the user wearing enhancer 110.

Thus, enhancer 110 tracks the motions of a user's lower extremities. Optimally in the powered state, the user only minimally feels enhancer 110 and any load supported by enhancer 110. Further, enhancer 110 does not significantly inhibit a user's movements, allowing the user a full range of motion in both the powered and the un-powered state.

Enhancer 110 may incorporate a number of "safety" features to protect both the user and enhancer 110. The range of motion of a particular joint may be limited so that the user cannot exceed the safe operational range, or to protect the user by preventing enhancer 110 or the user from exceeding a range of motion, which might harm the user. Enhancer 110 may include a balance control so that the user cannot unknowingly step too far beyond the center of gravity of enhancer 110 and the load. Safety features such as these could be implemented by feedback at the joints that increases the impedance of the joint as it approaches a dangerous position. Absolute limits of joint movement could also be determined by the design of the joint.

2. Joints

As described above, enhancer 110 includes multiple links connected at joints. In the present exemplary embodiment, two links can be connected with multiple joints. For example, shank links 124, 134 and foot links 162 are connected with multiple ankle joints 148, 150, where ankle joint 148 corresponds to a flexion/extension motion and ankle joint 150 corresponds to an abduction/adduction motion. In FIGS. 1 to 3, hip assembly 152 is shown with three hip joints 140, 142, and 144, corresponding to the abduction/adduction, rotation, and flexion/extension directions of motion. Various types of joints may be used to achieve the desirable range of motion. Examples of typical joints include but are not limited to: rotary joints, flexible joints, spring joints, and the like.

An example of a rotary joint is shown in FIG. 4A for left leg support 130 between thigh link 132 and shank link 134. The proximal end of shank link 134 and the distal end of thigh link 132 are coupled together in knee joint 146, which is a rotary joint. A rotary joint allows rotation in a given axis and deflects very little under the forces or moments about the other axes.

FIG. 4A illustrates an exploded view of knee joint 146. Knee joint 146 is assembled from the proximal region of shank link 134 and the distal region of thigh link 132, two bearing plates 410, an actuator mount 440, two sets of bearings 412, an encoder 420, and fasteners 430. In this example, shank link 134 is fastened to a bearing plate 410, which houses two bearings 412 that surround the distal end of thigh link 132. Bearings 412 movably contact the surface of the distal end of thigh link 132. In FIG. 4A, two complement bearings 412 are spaced one inch apart to minimize friction. Although bearings 412 shown are ball bearings, any bearings capable of withstanding the forces acting on the joint (moment) could be used, including wide brush or journal bearings. Sensors, such as encoders (rotational encoders), may be included in the joint design. The joint may include attachment site(s) for an actuator or actuators. In the present exemplary embodiment, knee joint 146 of right leg support 120 (FIG. 1) is a minor image of knee joint 146 of left leg support 130 (FIG. 1).

With reference to FIGS. 4B and 4C, knee joint 146 includes a mechanical stop surface 460 that limits rotation between thigh link 132 and shank link 134. The relative angle between thigh link 132 and shank link 134 is limited because the surface of the distal end of thigh link 132 will contact mechanical stop surface 460 on bearing plate 410. This limits the range of motion of knee joint 146 and can protect both knee joint 146 and the user. The position of mechanical stop surface 460 (e.g., the range of motion of knee joint 146) can be changed, for example, by altering the shape of bearing plate 410. Further, bearing plate 410 and surrounding structure (e.g., thigh link 132 in the example above) may be designed to enhance stop performance. For example, when knee joint 146 is bent to the extreme of its range of motion, bearing plate 410 and thigh link 132 can include parallel surfaces that contact each other with a large surface area. Also, a coating or protective layer (e.g., neoprene rubber) could be added to mechanical stop surface 460 to protect the surface and to reduce impact.

Figure 5A:
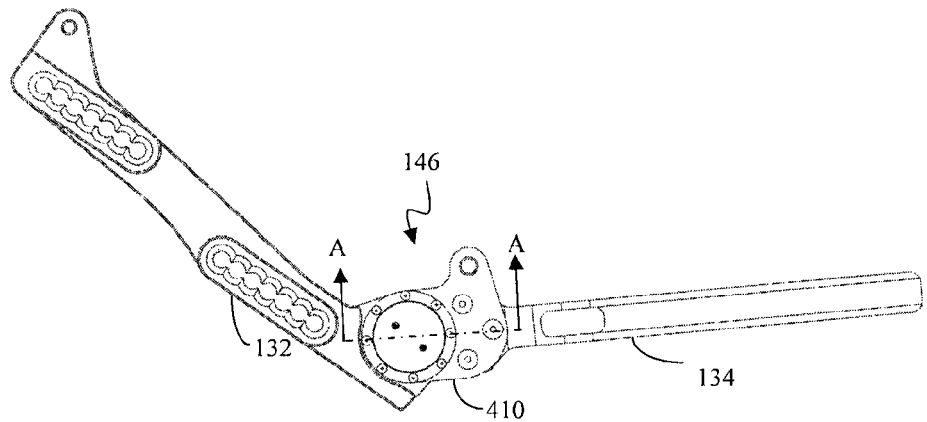
FIG. 5A is a schematic drawing of a jointed link for a knee region.
Figure 5B:
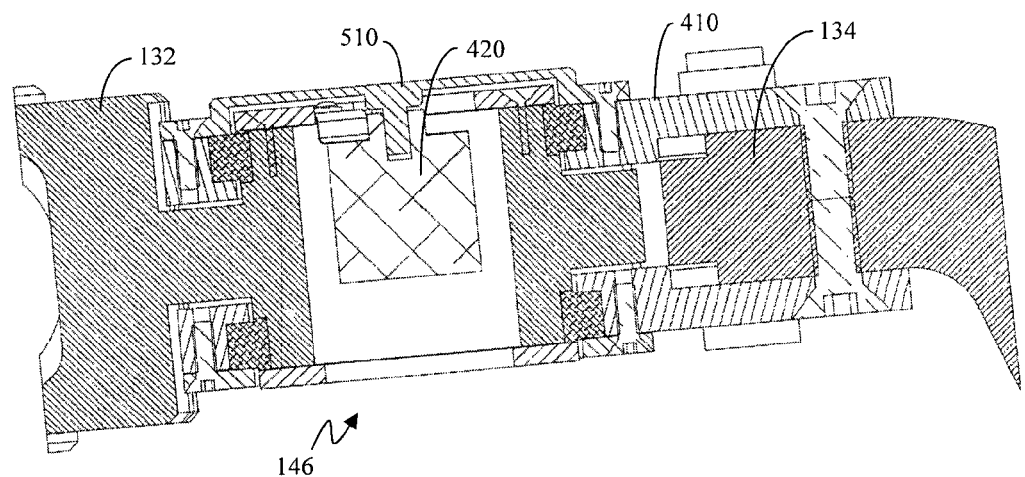
FIG. 5B is a section through the rotary joint (along the A-A plane) of FIG. 5A.

FIG. 5A is a schematic drawing of knee joint 146. A section through the knee joint 146 (along the A-A plane) is shown in FIG. 5B. Encoder 420 is mounted to thigh link 132 and held in position by an outer retaining ring 510. Other sensors for detecting position, movement, and forces acting on knee joint 146 could also be mounted at knee joint 146, thigh link 132, or shank link 134.

The materials chosen for the components of knee joint 146 should be appropriate for the functions of the joint. For example, the bearing plates should be made of a high-strength, low-weight material, such as Aluminum (e.g., 7075 Aluminum). Stronger materials such as Titanium may also be used, or used for other components of knee joint 146, such as the retaining rings for the bearings. These materials are offered as examples only; in general, the components of enhancer 110 (FIG. 1) can be made of any metal, alloy, polymer, ceramic, rubber, or other material or combination of materials with adequate mechanical, electrical, and chemical properties.

With reference to FIG. 1, other rotary joints may include additional components, or may omit some of the components shown in FIG. 4A. For example, joints that are not actuated will not require actuator mounts. Joints with a single bearing set may also be used. In addition, the loads seen by each jointed link will influence the design requirements of each joint. In general, joints that bear high forces (torsion, stress, strain) may include additional support or mechanical adaptations to help withstand these forces.

The orientation of a joint depends on the intended direction of motion for that joint. For example, the human knee moves in flexion and extension in the human's sagittal plane; thus knee joint 146 may also be configured to move in flexion and extension (in the user's sagittal plane). In another example, the human hip joint is capable of moving in rotation, flexion/extension, and abduction/adduction. Thus enhancer 110 can include a plurality of joints in different configurations to approximate these same movements. Although the joints described above are configured to move in only one plane (e.g., flexion/extension), other joint configurations could be used with enhancer 110. For example, joints configured to move in both rotation and flexion/extension, or joints configured to move in rotation, flexion/extension, and abduction/adduction, could all be used with enhancer 110.

Joints may be connected to an actuator or not connected to an actuator. In one exemplary embodiment, only joints moving in the flexion and extension direction (in the sagittal plane of a user) are powered by actuators.

3. Actuator

As described above, in the "powered" state, the powered joints are controllably moved by actuators 166. Actuators 166 can include but are not limited to: pressure-based actuators (e.g., hydraulic, pneumatic, etc.), electric actuators, thermal actuators, mechanical actuators, and hybrids and combinations of these. For the sake of simplicity, the examples described herein are hydraulic actuators; however, any actuator adaptable to apply force to a joint may be used, as will be apparent to one skilled in the art. Further, different kinds of actuators 166 may be used to apply force to different joints.

In one exemplary embodiment, linear hydraulic cylinders are used to actuate the ankle, knee, and hip joints. The forces applied at these joints may be relatively low for hydraulic actuators (a few hundred pounds), thus small-bore hydraulic cylinders with a supply pressure of approximately 1000 psi may be used. In one exemplary embodiment, the hydraulic actuator may have a long stroke length (e.g., 4-5 inches). Power for the hydraulic actuators could be supplied by hydraulic hoses connected to a central hydraulic pressure source (power source). Thus, enhancer 110 may include any of the components required to power and operate the hydraulic actuators. For example, servo-valves may be used to regulate hydraulic flow in and out of each cylinder. When other types of actuators are used, enhancer 110 may likewise be adapted to incorporate any of the components required.

The controller may be adapted to the different kinds of actuators used in different embodiments of enhancer 110. The controller controls the actuators, and thus may be calibrated to accurately command an actuator and coordinate its movement with the rest of enhancer 110 and the user. Thus, the controller may incorporate response parameters of each actuator, such as time response, energy requirements, force output, impedance, and the like.

Figure 6:
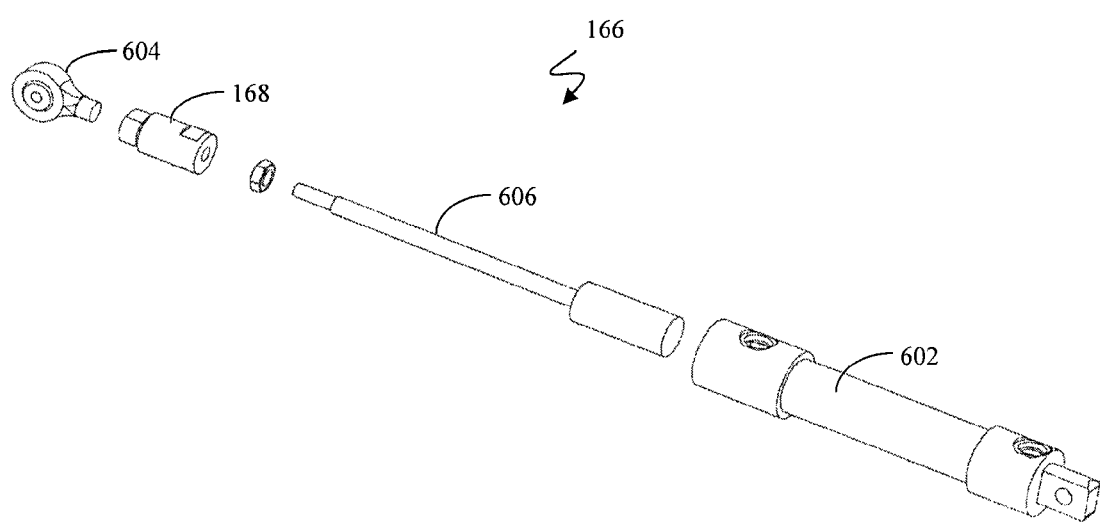
FIG. 6 is an exploded view of a hydraulic actuator.

FIG. 6 is an exploded view of a hydraulic actuator 166. A cylinder body 602 attaches to one region of a link (e.g., along the long axis of shank link 124, 134 (FIG. 1)), and a rod end 604 connects to the actuator mount portion of a bearing plate. A cylinder rod 606 can move within cylinder body 602 when a controller regulates the hydraulic pressure within cylinder body 602. Additional components may also be included as part of actuator 166, such as adaptors or sensor 168. In FIG. 6, force sensor 168 is included at rod end 604 before attachment to the bearing plate. Force sensor 168 may provide information used by the controller to detect forces (e.g., torques) acting at the joint.

4. Power Supply

With reference to FIG. 3, enhancer 110 may be powered by an on-board power source 302 or by an off-board power source. On-board power supplies are typically carried by enhancer 110 (e.g., on back frame 154). The power supply may be virtually any power source capable of driving the actuators. Thus, for hydraulic actuators, a power source may include a pump and an accumulator for generating and storing hydraulic pressure. Other pressure-driven actuators may likewise use other pump-based systems, including but not limited to: electric-motor driven pumps, internal combustion-engine pumps, or chemically-driven pumps. One example of a chemically-driven pump appropriate for enhancer 110 is a monopropellant-powered system in which $H_2O_2$ is catalytically reacted to produce oxygen gas and water vapor. The actuator power supply may be separate from power supplies running other components of enhancer 110 (e.g., the controller), or even other actuators. In one exemplary embodiment, the power supply is the same for all of the components of enhancer 110. In one exemplary embodiment, enhancer 110 includes a backup power supply. In one exemplary embodiment, the power supply is a battery.

5. Back Frame

In one exemplary embodiment, some portion of back frame 154 rigidly attaches to a user, either directly or though an intermediary, such as a harness. However, back frame 154 does not substantially interfere with the user's lower extremities and is configured to bear a load.

Back frame 154 has an outer side (facing away from a user) and an inner side (adjacent to a user). With reference to FIG. 2, back frame 154 may include sensors (for example, force sensors 174 to detect contact and forces between the user and enhancer 110, and inclinometer 208 to detect the angle of enhancer 110 relative to the ground) on any part of back frame 154. Back frame 154 may also include attachment sites for the power supply, additional equipment, a pack, or a load, preferably on the outer side of back frame 154. The inner side of back frame 154 may include a mount to attach to a user, such as straps or buckles.

Figure 7:
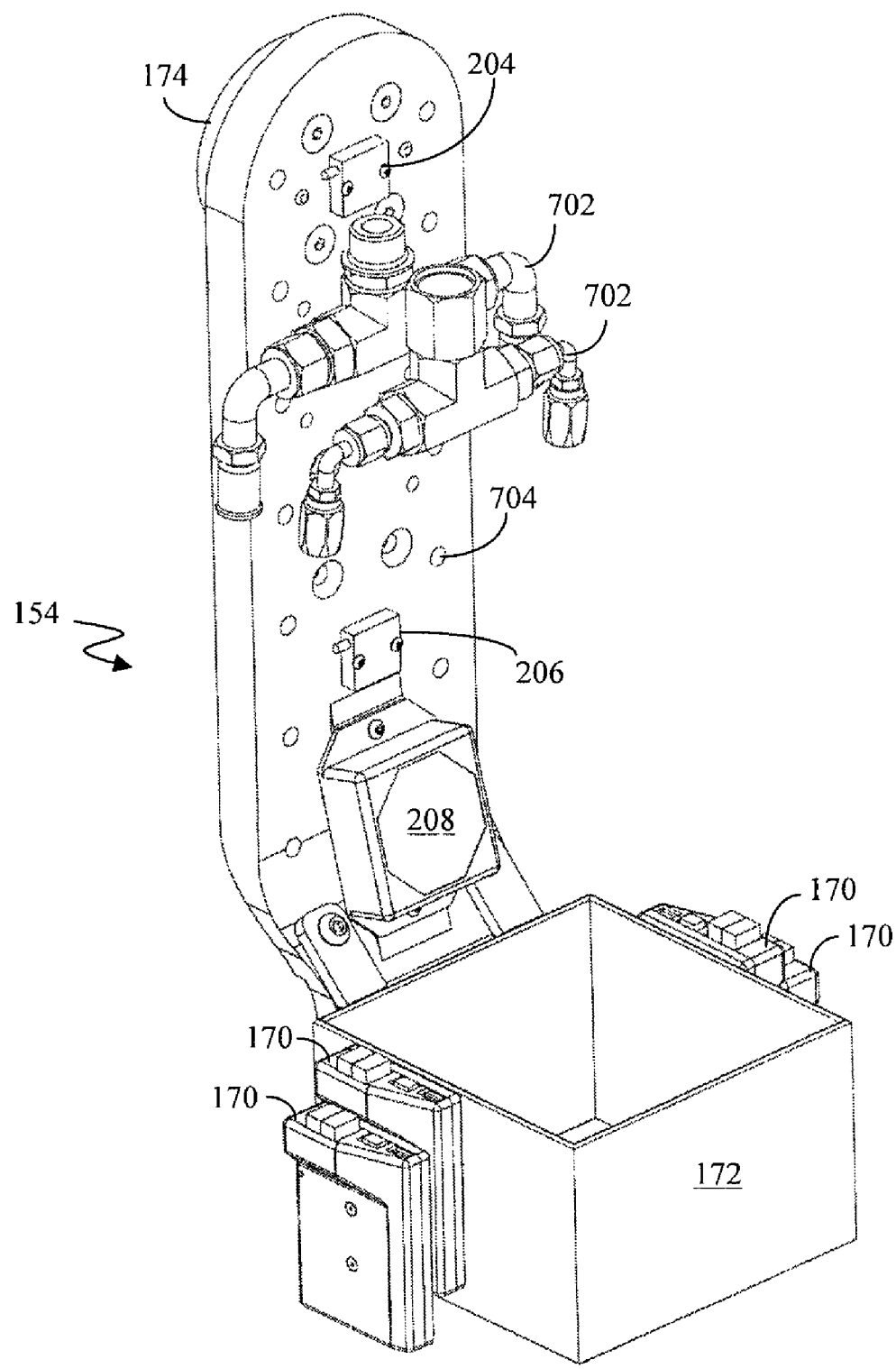
FIG. 7 is a schematic view of a back frame.

FIG. 7 shows a schematic example of the outer side of back frame 154. Back frame 154 has a housing 172 for the electronics (e.g., the controller and other electronics), mounted sensors (e.g., inclinometer 208 and force sensor 174), and hydraulic tees 702 for connecting the actuators to a hydraulic power source. Back frame 154 also includes holes 704 for mounting additional components. The lower portion of back frame 154 may also be integrally configured as hip assembly 152 (FIG. 1) that attaches to leg supports 120, 130 (FIG. 1). Alternatively, hip assembly 152 (FIG. 1) may be separable from back frame 154, and attach to it.

Figure 8A:
FIGS. 8A and 8B show a front and a back view of a detachable harness.
Figure 8B:
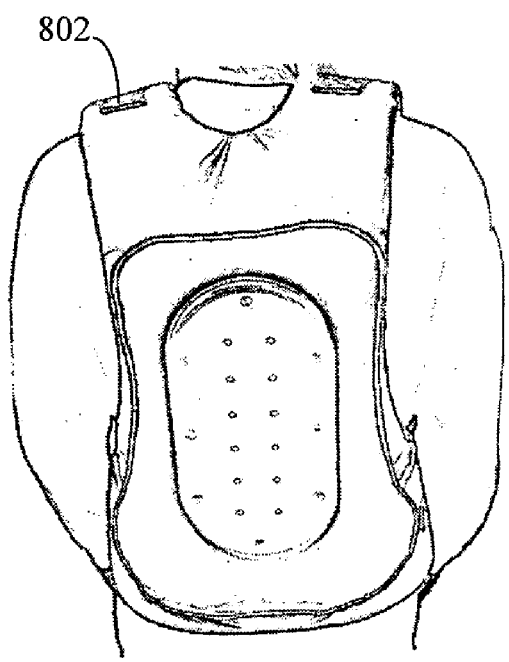

A harness configured to be worn by a user may also be part of back frame 154. The harness may be integral to back frame 154 or a detachable part. FIGS. 8A and 8B show an example of a detachable harness 802. FIG. 8A shows the front of harness 802 being worn around a user's torso. Harness 802 has straps that fit over a user's shoulders and around the user's waist, and can be adjusted to fit users of different sizes. FIG. 8B shows the back of harness 802 in FIG. 8A, which can removably attach to enhancer 110 (FIG. 1).

6. Hip Assembly

With reference to FIG. 1, as described above, the lower region of back frame 154 may be configured as hip assembly 152 for attachment to leg supports 120, 130. Alternatively, hip assembly 152 may be a separate region that attaches to back frame 154 in a rigid fashion.

Figure 9:
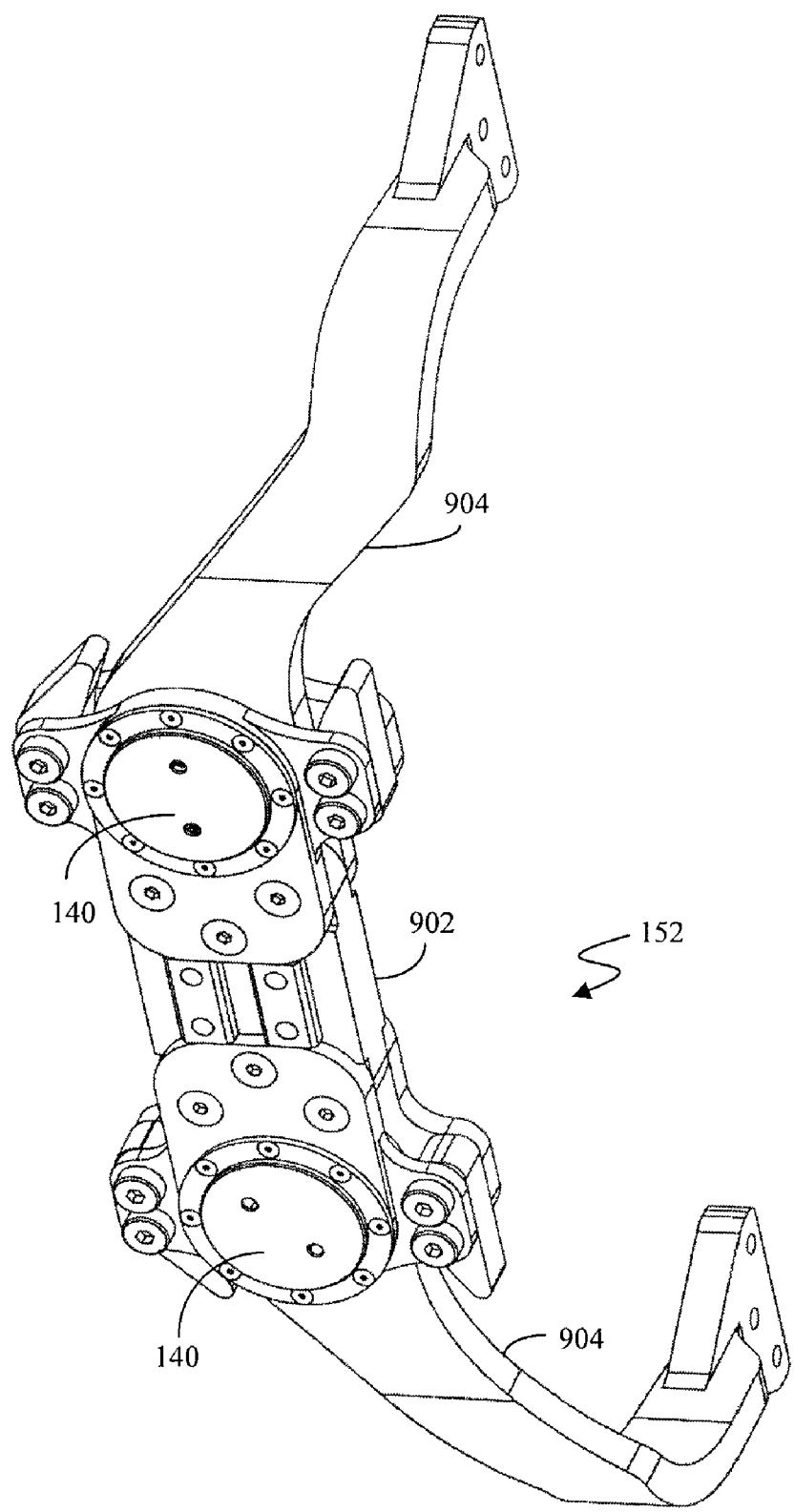
FIG. 9 is a schematic view of a hip assembly.

FIG. 9 shows a schematic view of one version of hip assembly 152. Hip assembly 152 includes connections between the links of the most proximal portions of leg supports 120, 130 (FIG. 1) and back frame 154 (FIG. 1). In FIG. 9, hip assembly 152 is also adjustable to allow users of different sizes to adjust enhancer 110 (FIG. 1) to fit their body morphology. The width of hip assembly 152 can be changed (corresponding to the user's girth), for example by swapping out a hip spacer 902 in the region between two hip joints 140. In one exemplary embodiment, hip spacer 902 is a lockable slider that can be moved to adjust the distance between hip joints 140.

In FIG. 9, hip joints 140 are part of the jointed link encompassing back frame 154 (FIG. 1) and hip spacer 902. In one exemplary embodiment, a hip range of motion includes abduction/abduction, rotation, and flexion/extension. In one exemplary embodiment, this range of motion may be achieved using three hip joints in series. FIG. 9 is one example of this range of motion, in which the hip assembly 152 includes a hip arc 904 on the right and left sides. Hip arcs 904 serve as segments of the jointed links; in FIG. 9, hip arc 904 is part of hip joint 140.

Figure 10:
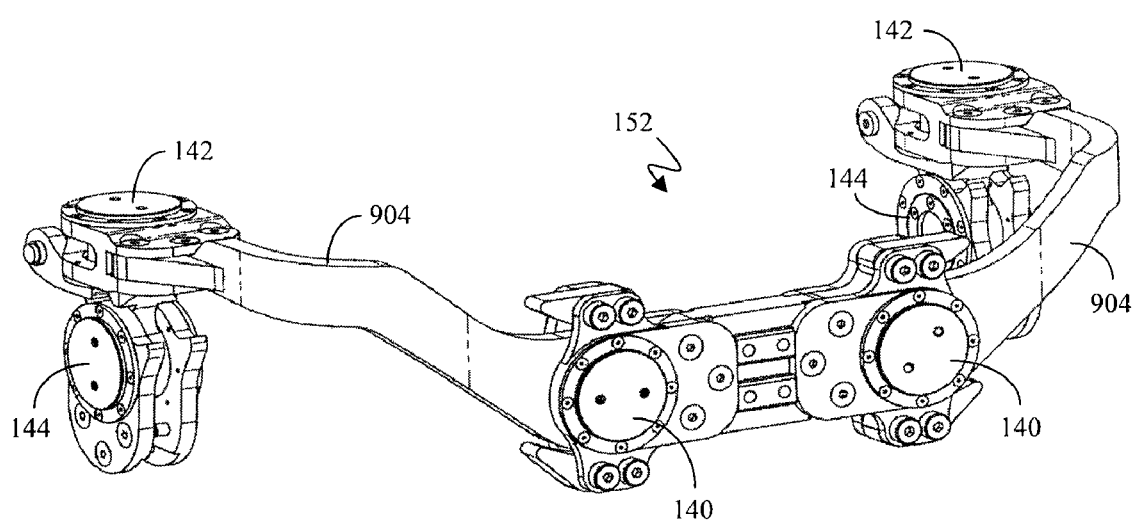
FIG. 10 is a schematic view of a hip assembly including jointed links for rotation and flexion/extension.

FIG. 10 shows a hip assembly 152 including jointed links for rotation and flexion/extension. Alternative arrangements of the joints attached at the hip are also possible.

Figure 11:
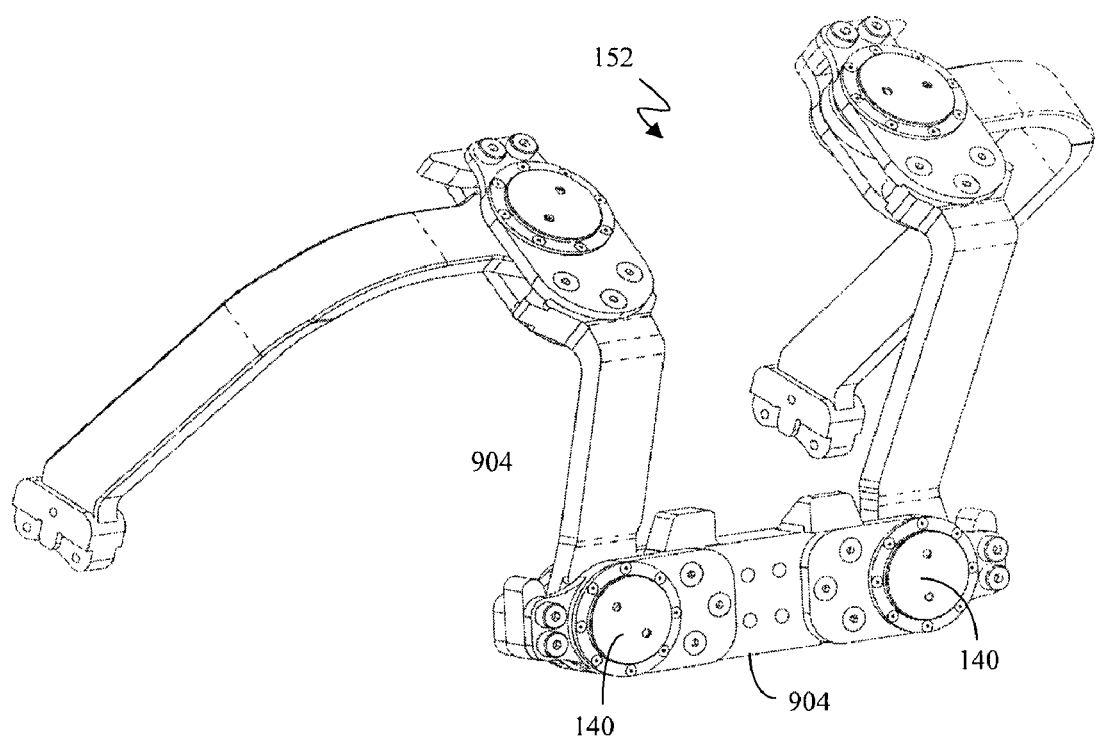
FIG. 11 is a schematic view of another hip assembly.

FIG. 11 is an alternative design of hip assembly 152 showing that the joints of enhancer 110 (FIG. 1) may be placed in any position that permits the user to move relatively unencumbered by the position of enhancer 110 (FIG. 1).

7. Thigh Links

With reference to FIG. 1, as described above, the proximal end of thigh links 122, 132 connect to hip assembly 152 or back frame 154. The proximal ends of thigh links 122, 132 and hip assembly 152 form a joint, and the distal part of thigh links 122, 132 and shank links 124, 134 form another joint. Overall, thigh links 122, 132 should be relatively rigid (relatively inflexible), although they may be adjustable.

Figure 12B:
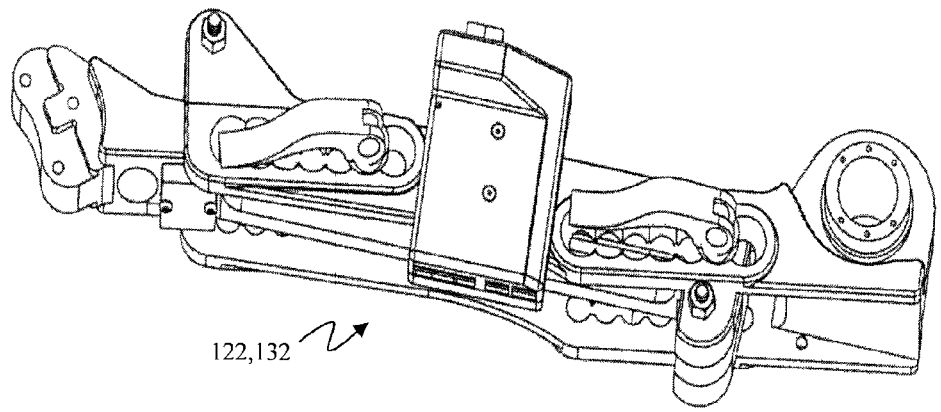
FIG. 12B is a schematic perspective view of a thigh link.
Figure 12A:
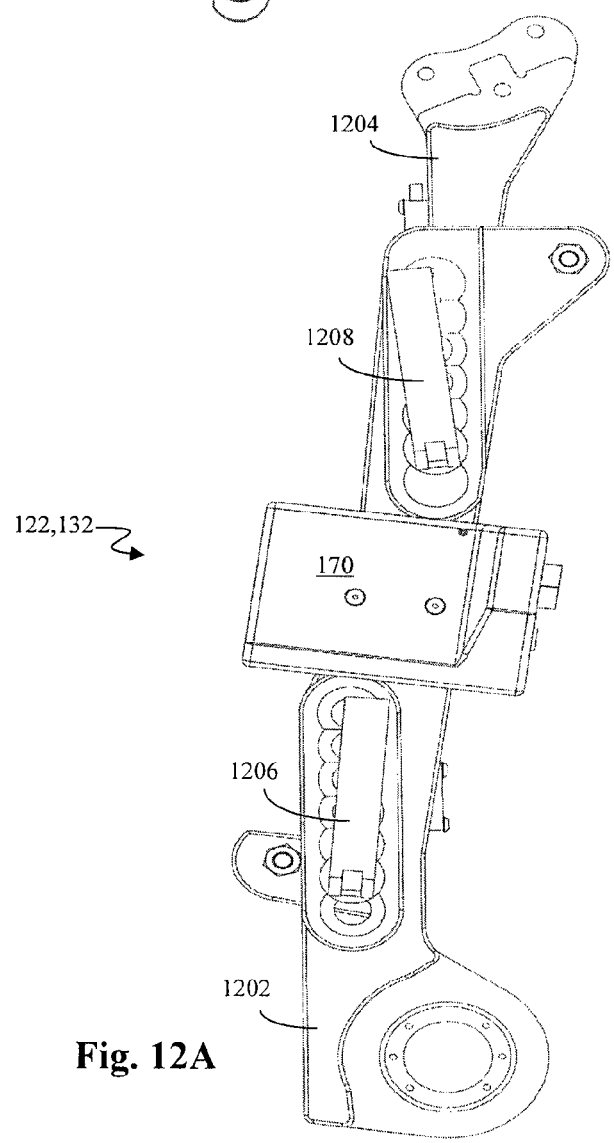
FIG. 12A is a schematic view of the side of a thigh link.

FIGS. 12A and 12B show one example of a thigh link 122, 132. In FIGS. 12A and 12B, the main structure of thigh link 122, 132 includes an outer piece 1202 and an inner piece 1204 that slide relative to each other for length adjustment. Outer piece 1202 attaches to knee joint 146 (FIG. 1) and actuator 166 (FIG. 1). Inner piece 1204 connects with hip joint 144 (FIG. 1) and actuator 166 (FIG. 1). Thus, thigh link 122, 132 may be adjusted to fit a variety of user sizes. FIGS. 12A and 12B also show a quick release mechanism for adjusting the length of thigh link 122, 132 in which two handles 1206, 1208 can be locked down to hold the adjusted inner and outer pieces 1204, 1202 in position.

In one exemplary embodiment, the region of thigh link 122, 132 that faces the user is kept substantially clear of components, reducing the chances that enhancer 110 (FIG. 1) will contact the user's leg or interfere with user mobility. In general, however, the other faces of thigh links 122, 132 (e.g., the outer faces) may include mountings for additional components such as sensors and controller components. In FIGS. 12A and 12B, a component is shown attached to the outer surface of thigh link 122, 132. Thigh link 122, 132 can also include attachments for power supply components (e.g., pneumatic, hydraulic, or electrical lines) and actuators.

8. Shank Link

Figure 13:
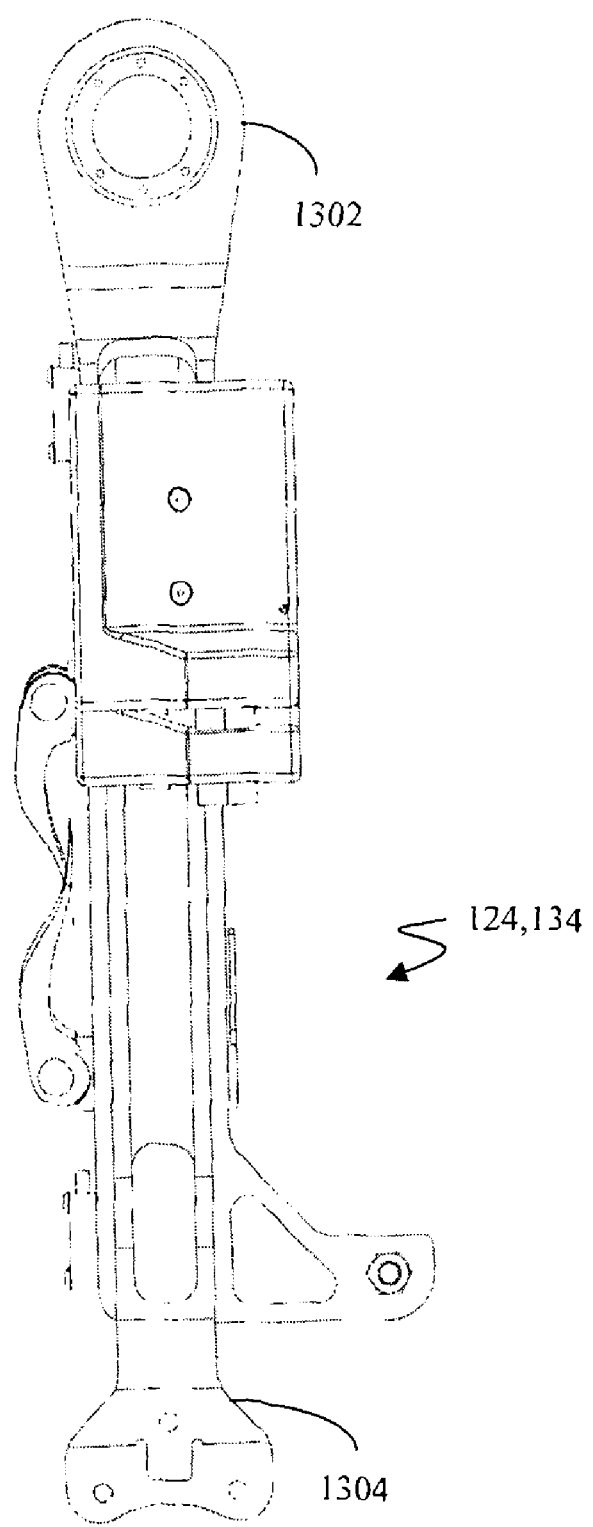
FIG. 13 is a schematic illustration of the side of a shank link.

With reference to FIG. 1, the distal end of shank links 124, 134 and foot link 162 form a joint at the ankle, and the proximal ends of shank links 124, 134 and the distal ends of thigh links 122, 132 form a joint at the knee. FIG. 13 shows an example of a shank link 124, 134. In FIG. 13, shank link 124, 134 has two straight pieces that can slide relative to each other, an outer shank 1302 and an inner shank 1304. Outer shank 1302 connects to ankle joint 148 (FIG. 1). The position of the inner and outer shanks 1304, 1302 can be adjusted to change the overall shank length based on the user's morphology, similar to the thigh adjustment described above. Also, the proximal and distal regions of shank link 124, 134 may be adapted to facilitate forming a joint. For example, in FIG. 13, the proximal region of inner shank 1304 is adapted to form a joint with thigh link 122, 132 (FIG. 1) by including a flattened, larger surface area for attachment to a rotary joint.

Figure 14:
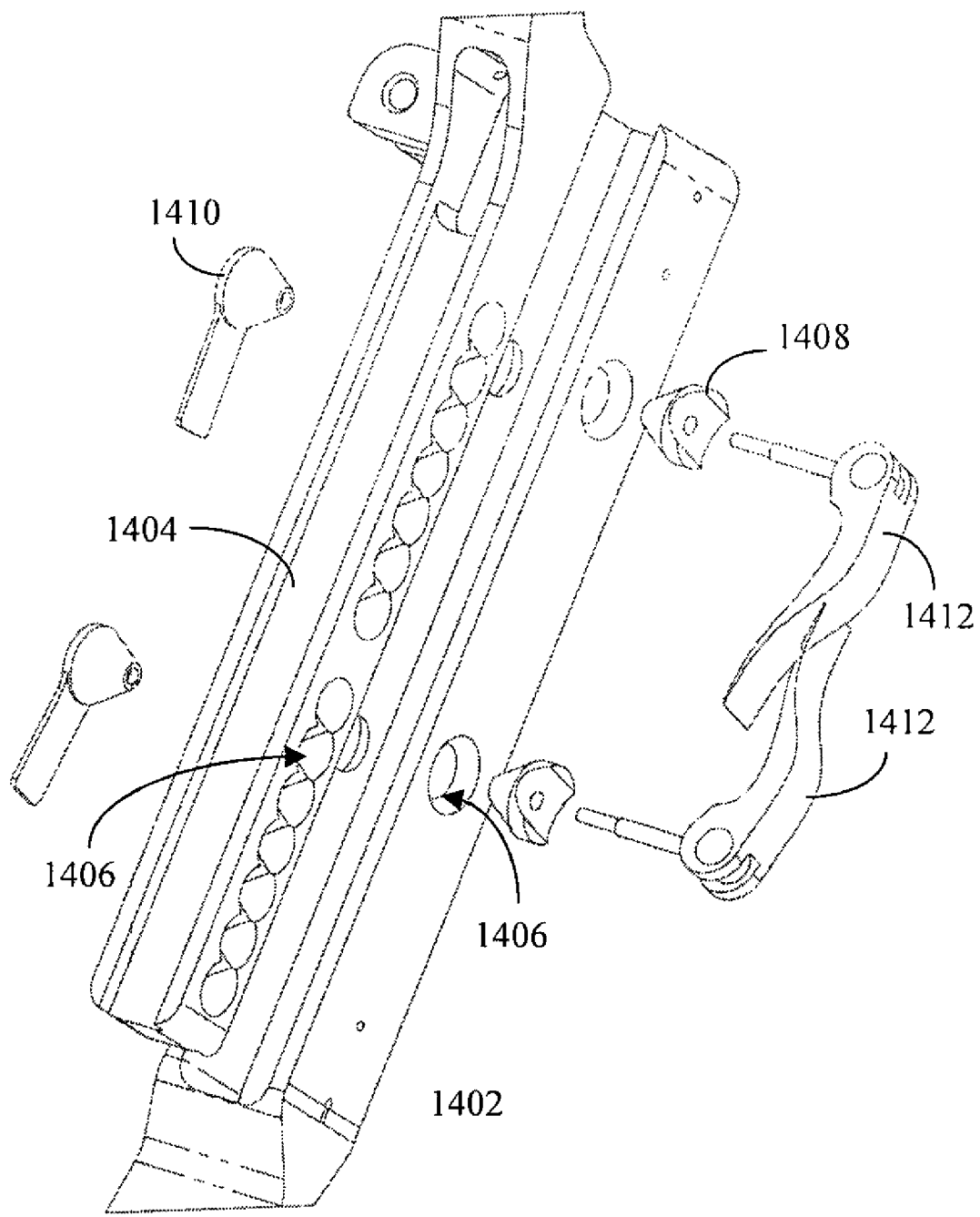
FIG. 14 is an exploded view of a shank and thigh adjustment mechanism.

FIG. 14 illustrates one exemplary embodiment of a shank and thigh adjustment mechanism. In FIG. 14, the link (shank link 124, 134 (FIG. 1) or thigh link 122, 132 (FIG. 1)) can be adjusted by quick-release clamps. Adjustment of shank links 124, 134 (FIG. 1) and thigh links 122, 132 (FIG. 1) is important for both versatility and user comfort. The quick-release mechanism shown is a simple method of adjustment. The link is shown with an outer link 1402 that is a U-shaped channel piece that slidably mates with an inner link 1404. Adjustment in the quick-release system is done in discrete intervals (based on the spacing of adjustment holes 1406). The link is locked into position by aligning the adjustment holes of the inner and outer links 1404, 1402, then screwing a threaded rod into a clamping cone 1408 on one side of a hole and a threaded cone 1410 on the opposite side. Pushing handles 1412 down then locks inner and outer links 1404, 1402 into position. Cones 1408 can be coated in (or fabricated from) a compressible material, such as rubber.

Figure 15:
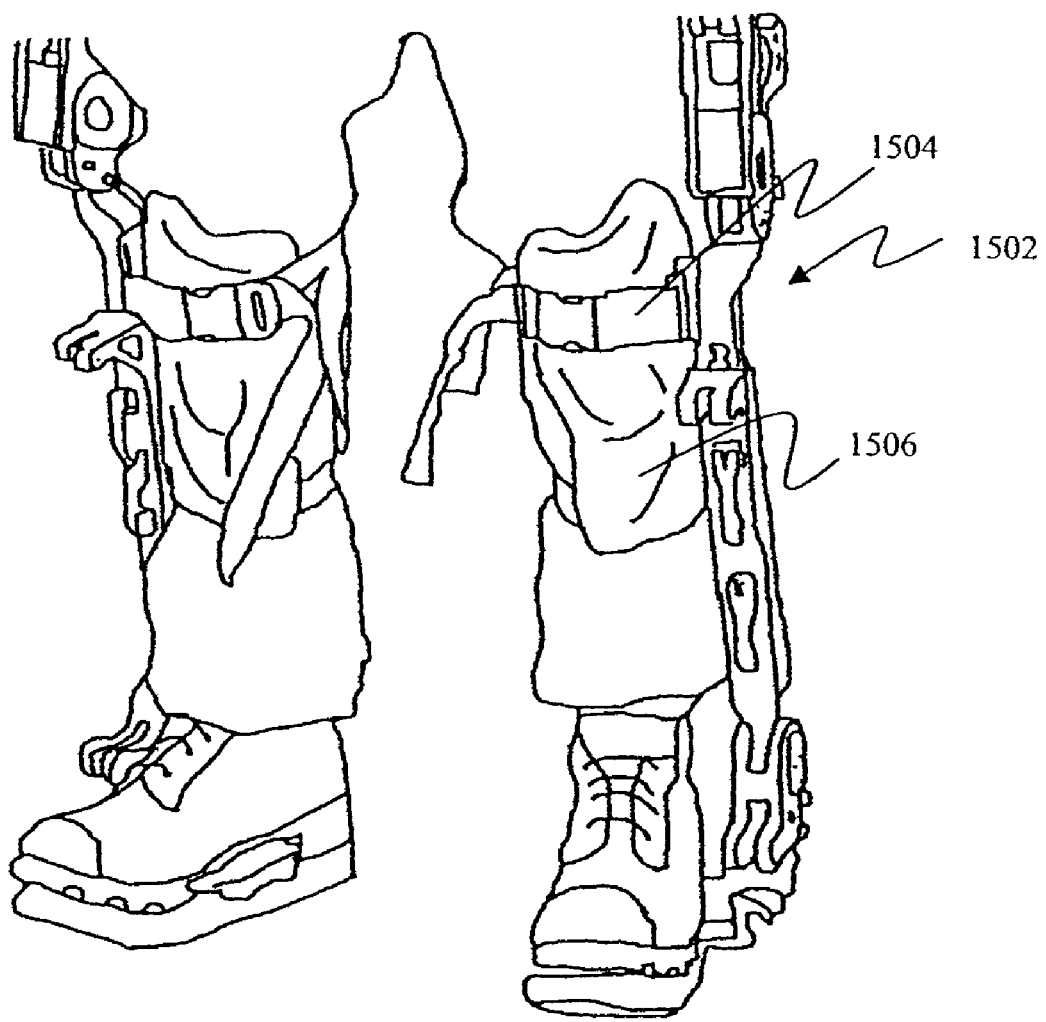
FIG. 15 illustrates a compliant shank attachment.

With reference to FIG. 1, shank link 124, 134 may also have additional attachment sites for other components of enhancer 110 (e.g., sensors or control system components). Shank link 124, 134 may also include a compliant attachment to connect to a user's lower leg to increase control over leg supports 120, 130. An example of this is shown in FIG. 15. Compliant attachment site 1502 may be adjustable, for example, by a strap or buckle system. In one exemplary embodiment, a compliant strap 1504 is buckled to a shin guard 1506 worn by the user.

9. Foot Links

With reference to FIG. 1, as described above, enhancer 110 has an ankle region formed by the joining of shank links 124, 134 and foot links 162. As also described above, foot links 162 rigidly attach to the user's feet. In addition, foot links 162 can include additional joints (e.g., to allow flexing/extension of the toes), connections to secure the user's feet, and sensors to detect contact with the ground, contact with the user, motion, etc.

Figure 16:
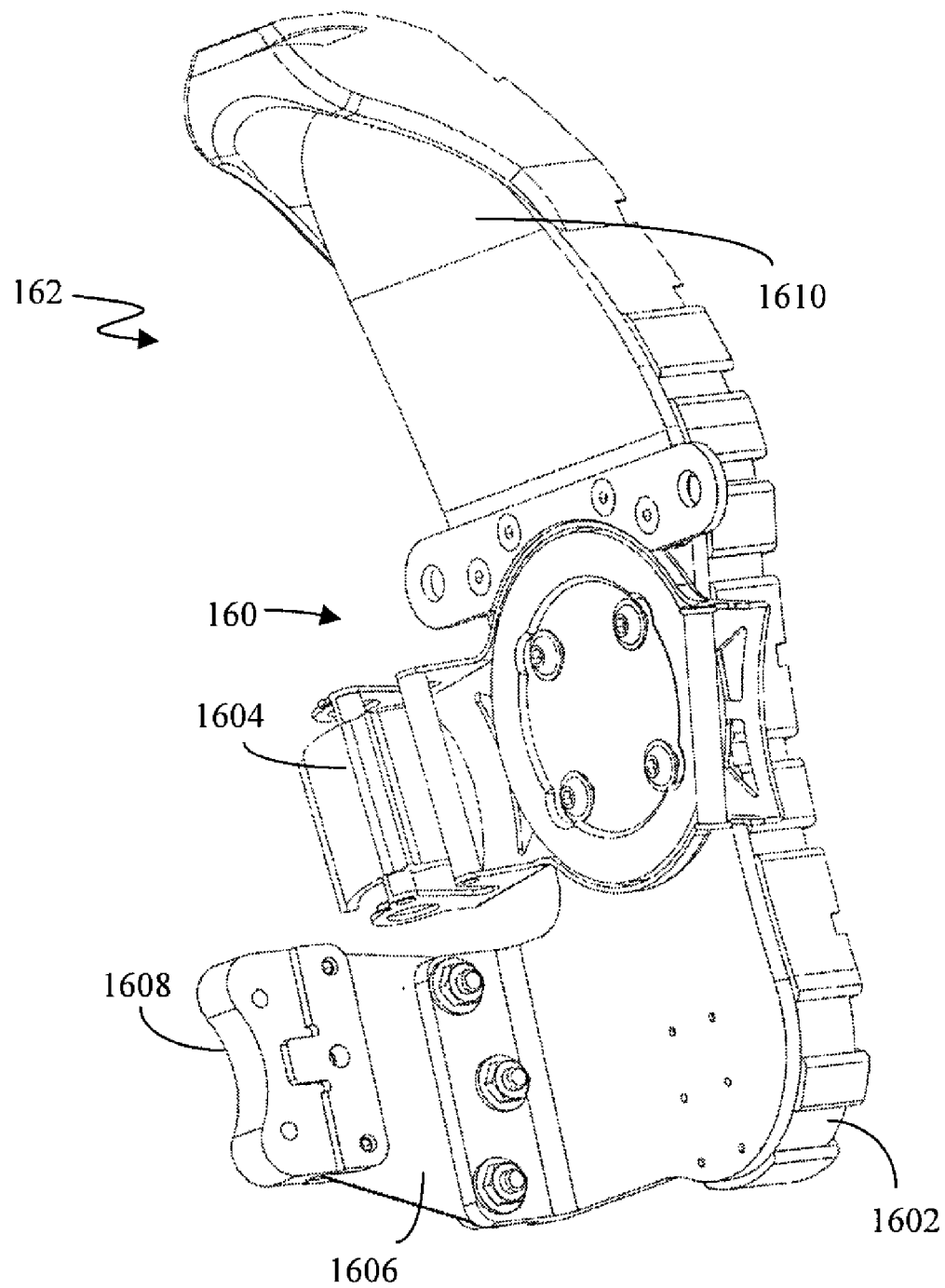
FIG. 16 is a schematic perspective view of a foot link.
Figure 17:
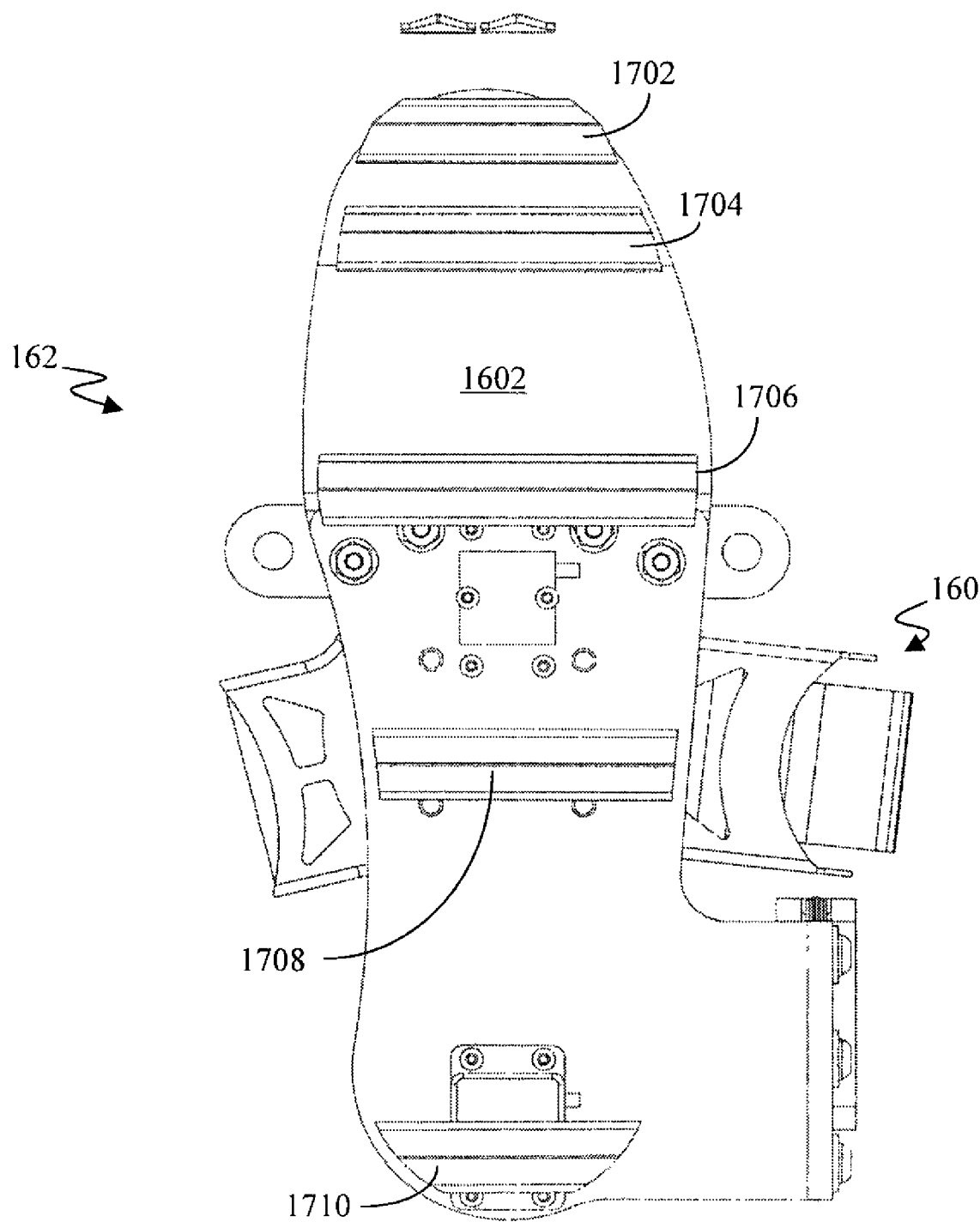
FIG. 17 is a schematic illustration of the sole of a foot link.

FIG. 16 is a schematic diagram of foot link 162, showing the side of sole 1602, foot bindings 1604, ankle sections 1606, 1608, and toe region 1610. With reference to FIG. 17, sole 1602 protects the components of foot link 162 while walking over rugged terrain, and may also house sensors. Sole 1602 is preferably molded from a durable and compliant material, such as a polymer (polyurethane, etc.) or other elastomer (e.g., rubber, etc.). If sole 1602 is somewhat compliant, it will help dampen unwanted impact spikes on the user and enhancer 110 (FIG. 1), as well as assisting enhancer 110 (FIG. 1) and the user in moving over varied terrain. Sole 1602 may also include a material, shape, or texture that helps with surface traction.

A plurality of sensors may be embedded in or integral to sole 1602. In FIG. 17, five touch sensors are embedded at tip 1702, toe 1704, ball 1706, middle 1708, and heel 1710. The touch sensors communicate with the control system and provide information on how foot link 162 is positioned on the ground. Sole 1602 may be formed of materials with different densities to help ensure that the touch sensors are depressed when a region of foot link 162 is in contact with the ground. In one exemplary embodiment, the area in sole 1602 around the touch sensors may be made of a less compliant material (e.g., higher-density polymer) than the rest of sole 1602 (e.g., a lower-density polymer).

Figure 18:
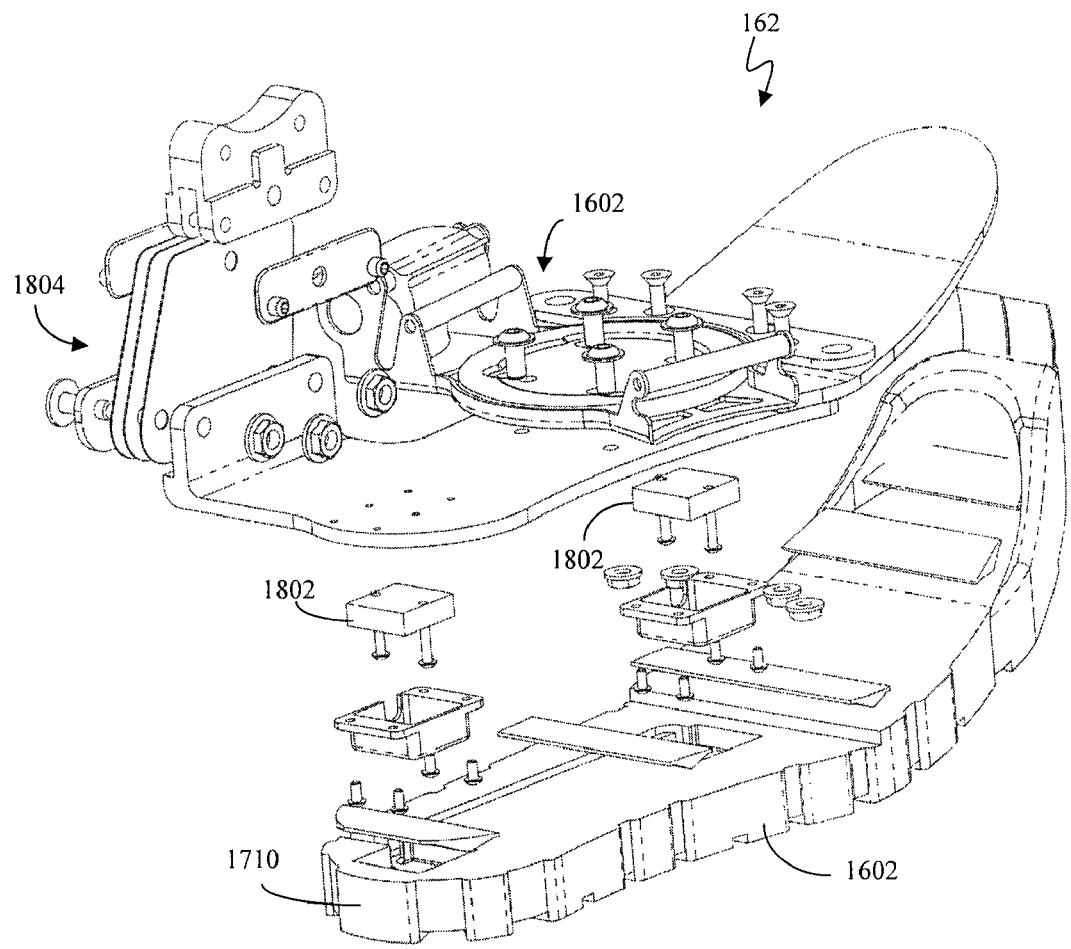
FIG. 18 is an exploded perspective view of a foot link.

With reference to FIG. 18, foot link 162 may also incorporate one or more accelerometers 1802. Accelerometers 1802 could be intrinsic to sole 1602 or mounted onto foot link 162 in some other region. For example, accelerometer 1802 may be bolted directly to heel 1710, and protected within a metal housing.

With reference to FIG. 17, sole 1602 is the most distal region of enhancer 110 (FIG. 1), and it may lie beneath a structural frame that supports the rest of foot link 162. Heel 1710 is rigid, and may be made of a rigid metal, such as aluminum. Heel 1710 forms a joint with toe 1704 and ball 1706 of foot link 162. This joint may be a flexible joint made, for example, of a compliant material, which allows slight bending of this joint as enhancer 110 (FIG. 1) follows the motion of the user. Thus, sole 1602, ball 1706, and toe 1704 may be made of compliant materials. The entire toe 1704 and ball 1706 region of the foot link 162 may be flexible.

Heel 1710 is also part of the ankle joint 148 (FIG. 1). With reference to FIG. 1, in one exemplary embodiment, two joints connect foot links 162 to shank links 124, 134: ankle joint 148 moves the ankle in flexion/extension, and ankle joint 150 moves the ankle in abduction/adduction. Ankle abduction/adduction may be accomplished through a spring joint, as shown in FIG. 18. The spring element eases the load on the user's ankles. In FIG. 18, the spring joint is shown as multiple compliant plates 1804 attached to heel 1710. Compliant plates 1804 may be made, for example, of steel or other appropriate spring material. Attached to the proximal end of the spring joint is a rotary joint for moving the ankle in flexion/extension. The ankle of enhancer 110 (FIG. 1) may have either a flexion/extension joint or an abduction/adduction joint, or both. In FIGS. 16 and 18, both joints are shown and are connected in series, potentially allowing greater flexibility.

As discussed above, the user is rigidly attached to foot links 162, and preferably, the user's foot is releasably bound to foot links 162. One exemplary embodiment of a releasable binding 160 is shown in FIGS. 16 and 18, and is modeled after a snowboard binding. For example, a Type-N click-in snowboard binding may be used. Ideally, the binding does not interfere with the bottom of the boot/shoe, and can easily be affixed to a standard boot/shoe. Other types of bindings, including snaps, belts, straps, buckles, and the like, may also be used. In one exemplary embodiment, the user's feet can be bound to foot links 162 without an additional shoe component. In one exemplary embodiment, the user's feet can be bound to foot links 162 without requiring the user to wear separate shoes.

10. Sensors

With reference to FIG. 1, enhancer 110 includes sensors for providing kinematic and dynamic data about the status of enhancer 110. Sensors may provide information about the joint angles and velocities of the joints, the acceleration of different regions of enhancer 110, the absolute foot angle of enhancer 110, the center of gravity of enhancer 110, and any forces acting on the joints and links of enhancer 110. These sensors are part of the control system (or systems) for enhancer 110. The control system may use this data to control the actuators and move enhancer 110.

In one exemplary embodiment, torque applied to a joint is measured at the joint by measuring the force at the actuator with force sensor 168. When the actuator is a hydraulic actuator, joint torque at the actuated joint may be measured by estimating the moment arm through the joint angle. Force sensor 168 may be included as part of the actuator mounting. In this arrangement force sensor 168 measures both the force applied by the actuator and the forces applied by the user and/or the environment on that joint. A rotary encoder may also be included as part of a link, to measure the relative angular position of the segments of each link. Preferably, a rotary encoder with a high resolution is used (e.g., approximately 40,000 counts/revolution). Such rotary encoders may also be used to measure absolute joint angle. Angular velocity may be calculated, as may acceleration of the joint.

In one exemplary embodiment, additional sensors directly measure parameters such as acceleration, avoiding excessive computation time, and increasing accuracy. For example, accelerometers may be included throughout enhancer 110, particularly at the joints and links. In one exemplary embodiment, linear accelerometers are used to measure acceleration of different regions of enhancer 110. For example, acceleration of shank links 124, 134 is measured by multiple accelerometers 202 (FIG. 2) mounted parallel to one another in the same sagittal plane of shank links 124, 134. Preferably, a pair of accelerometers is used to measure the acceleration of a region or body segment of enhancer 110. Angular acceleration (e.g., joint angular acceleration) can be obtained by measuring linear acceleration of two points a fixed distance apart on a region or body segment, such as accelerometers 204, 206 (FIG. 2) on back frame 154. Alternatively, a single rotary accelerometer may be used.

Sensors may also be used to detect the foot angle or foot contact between enhancer 110 and the ground. Contact sensors on the bottom of foot links 162 may be used to indicate the position of the foot with respect to the ground, such as toe contact, heel contact, etc. Force sensors may be used in place of, or in addition to, contact sensors to measure the ground forces acting on enhancer 110.

The position of the user or the torso of enhancer 110 with respect to gravity can be measured using one or more inclinometers 208. With reference to FIG. 7, in one exemplary embodiment, inclinometer 208 is mounted to back frame 154 to detect the angle of back frame 154. The control system may also use data from inclinometer 208 to detect joint angles from toe 1704 (FIG. 17), as well as the center of gravity of enhancer 110 (FIG. 1).

With reference again to FIG. 1, sensors could also be included to measure forces between the user and enhancer 110. For example, a multi-axis force/torque sensor 174 may be mounted on back frame 154 to measure forces between the user and enhancer 110.

Additional sensors may be included to provide feedback between enhancer 110 and the ground and/or the user. The control algorithms used by the control system may further refine the number and types of sensors used by enhancer 110. Enhancer 110 may also include sensors to detect parameters unrelated to force, position, velocity, and acceleration. Examples of other kinds of sensors which may be used in enhancer 110 include but are not limited to: temperature sensors, power-level detectors, weighted-load detectors, etc.

11. Control System

Figure 19:
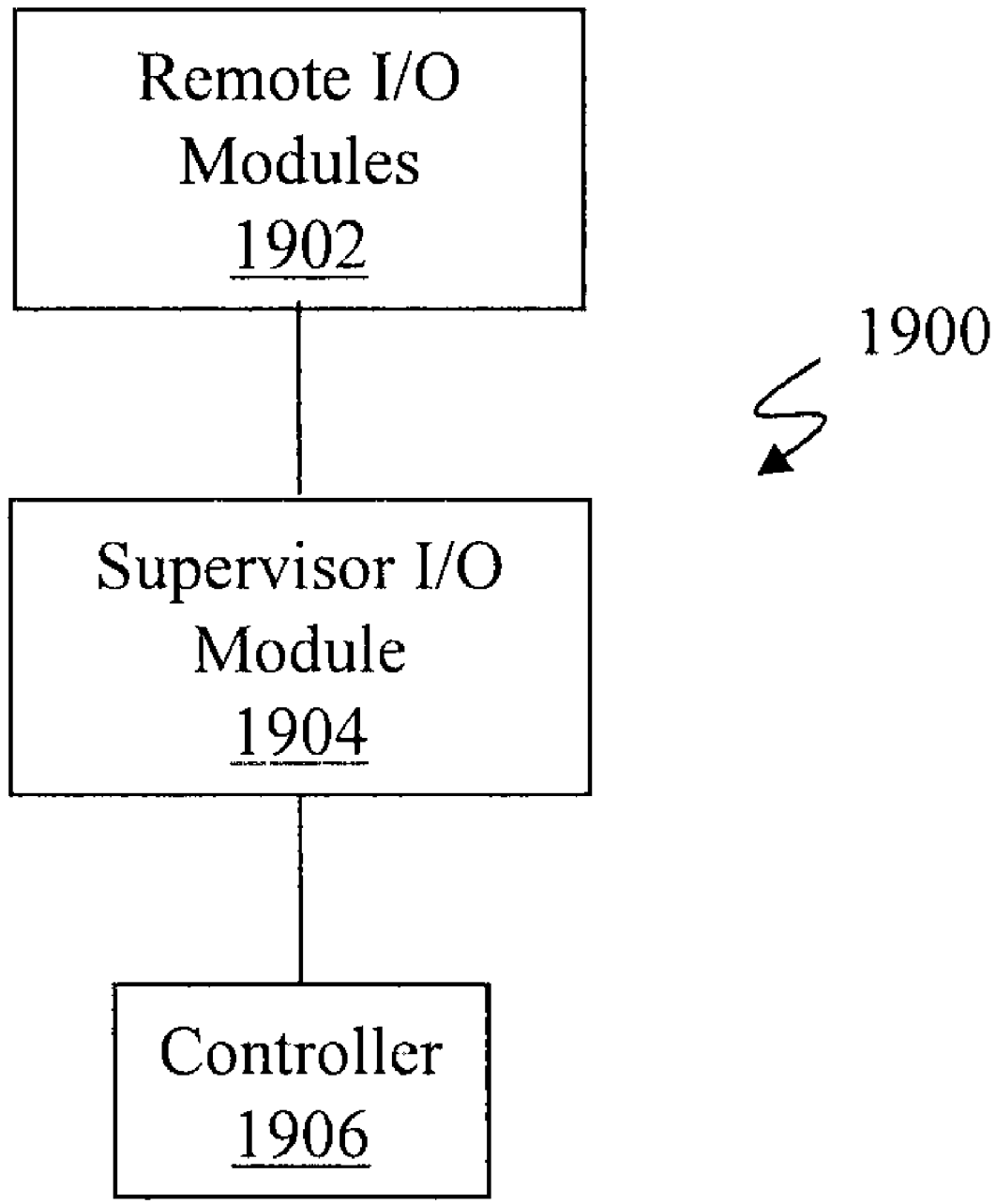
FIG. 19 is a block diagram of an exemplary control system.

With reference to FIG. 19, an exemplary control system 1900 is depicted. Exemplary control system 1900 includes remote or central Input/Output modules (RIOMs) 170, a supervisor I/O module (SIOM) 1902, and a controller 1904.

RIOMs 170 collect analog and digital sensor signals at different locations on enhancer 110 (FIG. 1). In one exemplary embodiment, each RIOM 170 includes three 14-bit±4V A/D converters, one encoder quadrature counter, six TTL digital inputs, and one 16-bit±5V D/A converter. Additionally, in the exemplary embodiment depicted in FIG. 1, two RIOMs 170 are disposed on each shank link 124, 134. One RIOM 170 is disposed on each thigh link 122, 132. Four RIOMs 170 are disposed on hip assembly 152. It should be recognized, however, that any number of RIOMs 170 can be disposed at various locations on enhancer 110.

With reference again to FIG. 19, RIOMs 170 are connected to SIOM 1902 in two chain-like structures using 200 Mbps digital communication lines and power supply lines. SIOM 1902 transmits data between RIOMs 170 and controller 1904, such as through a parallel I/O bus, a PCI board, and a PCI interface.

In one exemplary embodiment, controller 1904 is a single board computer (SBC), such as a Cool RoadRunner II PC/104-Plus SBC with a National Semiconductor Geod GX1 300 MHz processor. SIOM 1902 and controller 1904 can be disposed within housing 172 (FIG. 1). It should be recognized, however, that controller 1904 can be a series of distributed computers/processors rather than an SBC.

In one exemplary embodiment, controller 1904 is capable of being modifiably "programmed" to output appropriate actuator responses based on data received from the sensors. The controller is pre-programmed to output actuator responses based on sensor input data.

In one exemplary embodiment, controller 1904 implements a master control algorithm (the Supervisor task). The algorithm calculates required torques to be applied at each powered joint, and issues command signals to the controllable actuators, e.g., by sending a current to a hydraulic servo-valve corresponding to the force to be applied by the hydraulic actuator. The algorithm loop speed is determined by a counter (e.g., 2 kHz counter) signal. Thus, the sampling rate for this version of enhancer 110 (FIG. 1) is 2 kHz. Faster or slower sampling rates may also be used. Preferably, sampling rates are faster than 60 Hz (twice the frequency content of normal walking) and more preferably faster than 600-1200 Hz.

In one exemplary embodiment, in the powered mode, controller 1904, and in particular the master control algorithm running on controller 1904, ensures that enhancer 110 (FIG. 1) moves in concert with the user with minimal interaction forces between the user and enhancer 110 (FIG. 1). The algorithm ensures that the external forces on both the user and enhancer 110 (FIG. 1) are similar, but scaled appropriately to their masses. The algorithm ensures that the device-ground reaction forces are proportional to the user-ground reaction forces, and that the centers of gravities of the user and enhancer 110 (FIG. 1) move together. The algorithm regulates the torque applied at the powered joints.

In particular, with reference to FIG. 1, the human gait cycle may be divided into a stance phase (in which one or both leg supports 120, 130 support the user's weight) and a swing phase (in which a leg is out of contact with the ground, preparing for the next step). These phases may be further broken down into parts (e.g., heel strike, toe-off, etc.), during which the forces acting on the legs may be determined, including the forces acting on different regions of the legs. Enhancer 110 may use the position of the user's legs to help determine enhancer motion. The algorithm running on controller 1904 (FIG. 19) may thus estimate the appropriate force to be applied at a region (or joint) of enhancer 110 in order to allow a user to walk relatively unencumbered while carrying a load with enhancer 110.

The algorithm running on controller 1904 (FIG. 19) regulates actuators 166, causing them to track a desired force. The algorithm determines the appropriate force to be applied at each actuator 166 by processing input from sensors, and applying these measurements to control each actuator 166. The algorithm coordinates all actuators 166 of the powered joints so that actuator 166 moves without hindering the movements of the user.

With reference again to FIG. 19, in one exemplary embodiment, the algorithm running on controller 1906 processes joint variables such as joint angle, joint velocity, and joint force. The algorithm calculates the appropriate forces to be applied by the actuators knowing these variables. For example, a given actuator should apply force at a joint so that there is not a significant requirement for user-applied force in order to move a link. Thus, the user is not significantly encumbered by the impedance (or resistance) due to enhancer 110 (FIG. 1) as the user moves. The more powered joints that enhancer 110 (FIG. 1) has, the less the user will be encumbered, although the computational time for the algorithm may increase.

With reference to FIG. 1, in one exemplary embodiment, the algorithm running on controller 1904 (FIG. 19) processes forces applied by the user's foot and the forces applied by the ground on foot links 162. The algorithm (FIG. 19) then calculates the forces applied at the joints based on the ground forces at each foot link 162. Since only a user's back and feet are rigidly attached to enhancer 110, enhancer 110 may be controlled by measuring only the ground forces at foot link 162, rather than each individual joint.

The algorithm running on controller 1904 (FIG. 19) may also incorporate routines to save energy and to protect the user and enhancer 110. For example, power conservation may be achieved by allowing passive forces to actuate the one or more jointed links during some phases of motion (e.g., the swing phase). Safety features may include virtual limits on motion that passively warn a user before the user exceeds the margins of safety in operating the device. For example, enhancer 110 may increase the impedance (resistance to motion) when the user approaches a motion that exceeds some safe boundary.

Enhancer 110 may also include an interface for external input or output (e.g., by telemetry or by attaching a cable). Such an interface may allow diagnostic testing, reprogramming, debugging, and the like. Remote monitoring may also be included.

In summary, enhancer 110 described herein may be used to assist a user in carrying loads. Enhancer 110 may achieve many advantages not realized with other devices intended to aid users in carrying loads. In particular, enhancer 110 described herein allows a user to move while carrying a heavy load, substantially unencumbered by enhancer 110, even in the un-powered state.

Although the above examples have described various exemplary embodiments of enhancer 110 using primarily hydraulic actuators, enhancer 110 described herein may be actuated by any actuator acting on any number of joints. It will be appreciated by persons skilled in the art that numerous variations and/or modifications may be made to the described device as specifically shown here without departing from the spirit or scope of that broader disclosure. The various examples are, therefore, to be considered in all respects as illustrative and not restrictive.

We claim:

1. A lower extremity enhancer to be worn by a user, the enhancer comprising:
   two leg supports, each having a shank link and thigh link;
   a back frame connected to proximal ends of the leg supports;
   two foot links connected to distal ends of the leg supports; and
   a plurality of mechanical actuators configured to apply torques to the leg supports,
   wherein each foot link is rotatably jointed to a shank link of each leg support by a spring joint and configured to move in abduction and adduction.

2. The lower extremity enhancer of claim 1 wherein the spring comprises a compliant plate.

3. The lower extremity enhancer of claim 1 wherein the leg supports may be separable from the back frame.

4. The lower extremity enhancer of claim 1 wherein the shank links and thigh links incorporate adjustment mechanisms to shorten or extend their lengths.

5. A lower extremity enhancer to be worn by a user to, the enhancer comprising:
   leg supports, each leg support having a shank link and thigh link;
   a back frame connected to proximal ends of the leg supports;
   two foot links connected to distal ends of the leg supports; and
   a plurality of mechanical actuators configured to apply torques to the leg supports,
   wherein the lower extremity enhancer is configured to operate in both an unpowered and powered state.

6. The lower extremity enhancer of claim 5 wherein when the lower extremity enhancer operates is an unpowered state, it allows the user to move while carrying a heavy load substantially unencumbered by the enhancer.

7. A lower extremity enhancer to be worn by a user, the enhancer comprising:
   two leg supports having a plurality of jointed links;
   a back frame connected to proximal ends of the leg supports;
   two foot links connected to distal ends of the leg supports;
   a plurality of mechanical actuators configured to apply torques to the leg supports; and
   a controller, wherein the controller controls the mechanical actuators so that the user cannot unknowingly step too far beyond the center of the gravity of the enhancer and the load.

8. The lower extremity enhancer of claim 7 wherein the controller increases the impedance of the lower extremity enhancer when the user approaches a motion that exceeds some safe boundary.

9. A lower extremity enhancer to be worn by a user, the enhancer comprising:
- two leg supports having a plurality of jointed links;
- a back frame connected to proximal ends of the leg supports;
- two foot links connected to distal ends of the leg supports;
- a plurality of mechanical actuators configured to apply torques to the leg supports; and
- a controller to control the mechanical actuators,
- wherein the controller controls the mechanical actuators by estimating the appropriate forces to be applied at a region or point of the lower extremity enhancer in order to allow the user to walk relatively unencumbered while carrying a load.

10. The lower extremity enhancer of claim 9 wherein the controller processes joint variables, including joint angle and joint velocity, to calculate the appropriate forces to be applied by the mechanical actuators so the user is not encumbered by the enhancer's impedance.

11. The lower extremity enhancer of claim 9 wherein the controller processes joint variables, including joint angle and joint velocity, to calculate the appropriate forces to be applied by the mechanical actuators to reduce impedance of the lower extremity enhancer.

12. The lower extremity enhancer of claim 9 wherein the controller processes the forces applied by the ground on the foot links to calculate the appropriate forces to be applied by the mechanical actuators to reduce impedance of the lower extremity enhancer.

13. The lower extremity enhancer of claim 9 wherein the controller processes the forces applied by the user's feet on the foot links to calculate the appropriate forces to be applied by the mechanical actuators to reduce impedance of the lower extremity enhancer.

14. The lower extremity enhancer of claim 9 wherein the actuators cause the enhancer to track the motion of the user's lower extremities.

15. The lower extremity enhancer of claim 9 wherein the controller increases impedance of the lower extremity enhancer when the user approaches a motion that exceeds a safe boundary.

16. The lower extremity enhancer of claim 9 wherein the controller uses the position of the user's leg to determine the motion of the lower extremity enhancer.

17. The lower extremity enhancer of claim 9 wherein the one or more joints of the leg support are actuated passively during swing phase.

18. The lower extremity enhancer of claim 9 wherein the controller includes an interface for remote monitoring.

19. The lower extremity enhancer of claim 9 wherein the controller regulates the torque applied by the mechanical actuators.

20. The lower extremity enhancer of claim 9 wherein the back frame further includes a force/torque sensor and the controller processes the measured forces to calculate the appropriate forces to be applied by the mechanical actuators to reduce impedance of the lower extremity enhancer.

* * * * *